(12) United States Patent
Bachinski et al.

(10) Patent No.: US 9,211,400 B2
(45) Date of Patent: Dec. 15, 2015

(54) ELECTRODES, ELECTRODE SYSTEMS, AND METHODS OF MANUFACTURE

(75) Inventors: Thomas Jerome Bachinski, Lakeville, MN (US); Michael Moore, Oceanside, CA (US); Jay Dave, San Marcos, CA (US); Joseph Winn, Aliso Viejo, CA (US)

(73) Assignee: EMPI, Inc., St. Paul, MN (US)

( * ) Notice: Subject to any disclaimer, the term of this patent is extended or adjusted under 35 U.S.C. 154(b) by 281 days.

(21) Appl. No.: 13/446,832

(22) Filed: Apr. 13, 2012

(65) Prior Publication Data

US 2013/0023816 A1    Jan. 24, 2013

Related U.S. Application Data

(60) Provisional application No. 61/508,874, filed on Jul. 18, 2011.

(51) Int. Cl.
*A61N 1/04* (2006.01)
*A61N 1/32* (2006.01)
*A61B 5/0408* (2006.01)
*H01R 11/30* (2006.01)

(52) U.S. Cl.
CPC ............... *A61N 1/048* (2013.01); *A61N 1/044* (2013.01); *A61N 1/0456* (2013.01); *A61N 1/0492* (2013.01); *A61N 1/325* (2013.01); *A61B 5/0408* (2013.01); *A61B 5/04085* (2013.01); *A61B 5/04087* (2013.01); *A61B 2562/125* (2013.01); *A61B 2562/227* (2013.01); *H01R 11/30* (2013.01); *H01R 2201/12* (2013.01); *Y10T 29/49155* (2015.01)

(58) Field of Classification Search
CPC ... A61N 1/0428; A61N 1/0448; A61N 1/325; A61N 1/30; A61N 1/0492; A61N 1/045; A61N 1/0456; A61N 1/32; A61N 1/048; A61N 1/044; A61N 1/0424
USPC .................................... 604/19–21; 607/2–3
See application file for complete search history.

(56) References Cited

U.S. PATENT DOCUMENTS

| | | | |
|---|---|---|---|
| 4,543,958 A | 10/1985 | Cartmell | |
| 4,736,752 A | 4/1988 | Munck et al. | |
| 5,169,384 A * | 12/1992 | Bosniak et al. | 604/20 |
| 2001/0023330 A1 * | 9/2001 | Palti | 604/20 |
| 2004/0138712 A1 * | 7/2004 | Tamarkin et al. | 607/3 |

(Continued)

FOREIGN PATENT DOCUMENTS

WO    WO 2011/078071 A1    6/2011

*Primary Examiner* — Aarti B Berdichevsky
*Assistant Examiner* — Laura Schell
(74) *Attorney, Agent, or Firm* — Knobbe Martens Olson & Bear, LLP

(57) ABSTRACT

Multilayer electrodes, electrode systems, and stimulation systems are disclosed. An electrode may include a conductive layer with a unitary tail, a connector disposed on a distal end of the tail, and a nonconductive top layer disposed along a top portion of the conductive layer. An electrode may include a magnetic lead connector socket, or a receptacle formed by a depression in the conductive layer configured to receive a male connector. An electrode system may include a plurality of conductive zones and a plurality of connectors. A stimulation system may include an electronics layer in electrical contact with a conductive layer via a puncture connection, and may provide an iontophoretic treatment followed by a TENS treatment. Other electrodes, systems and methods are also disclosed.

14 Claims, 21 Drawing Sheets

(56) References Cited

U.S. PATENT DOCUMENTS

| | | |
|---|---|---|
| 2005/0215872 A1* | 9/2005 | Berner et al. .............. 600/347 |
| 2006/0036209 A1* | 2/2006 | Subramony et al. .......... 604/20 |
| 2008/0050984 A1 | 2/2008 | Ehr et al. |
| 2008/0132772 A1 | 6/2008 | Lang et al. |
| 2008/0221631 A1 | 9/2008 | Dupelle |
| 2008/0221632 A1 | 9/2008 | Bardy et al. |
| 2009/0112283 A1* | 4/2009 | Kriksunov et al. ............ 607/46 |
| 2012/0330217 A1 | 12/2012 | Hasui |

* cited by examiner

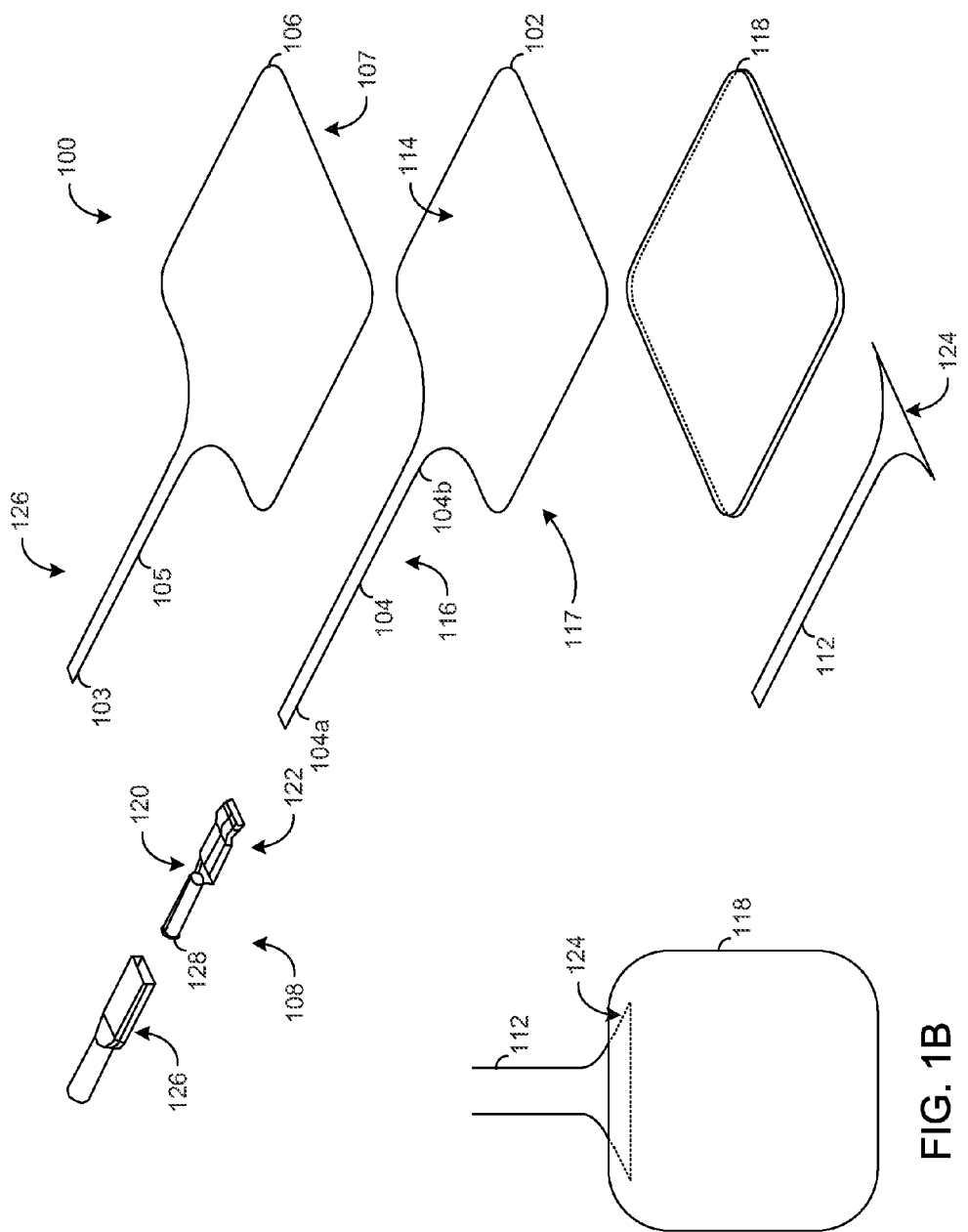

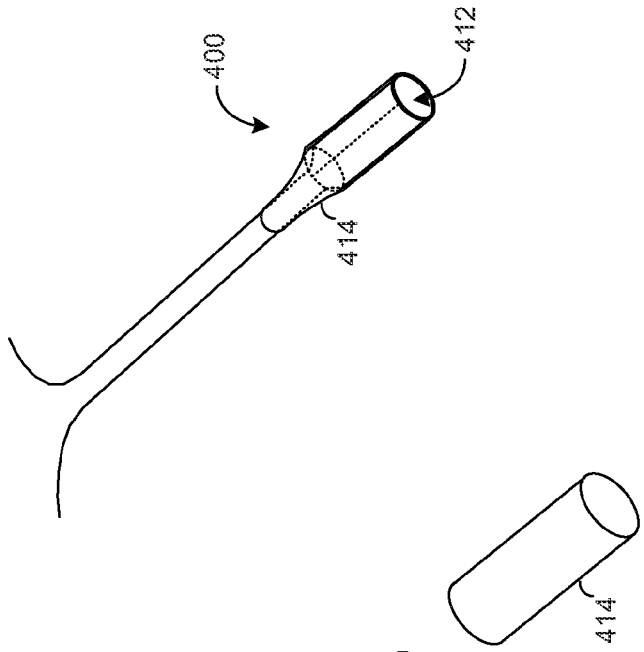
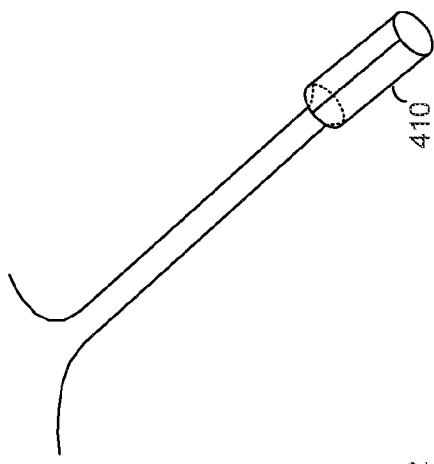
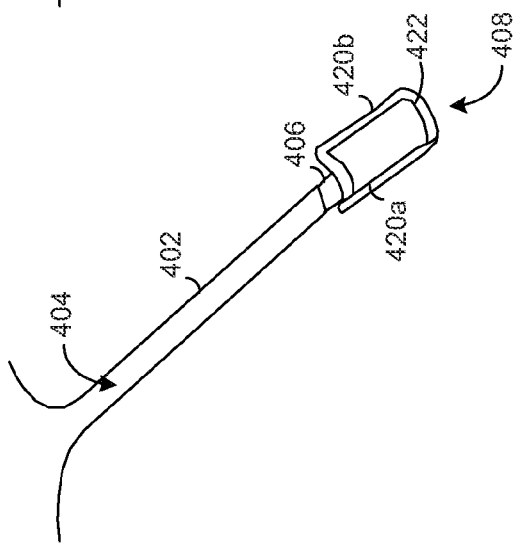

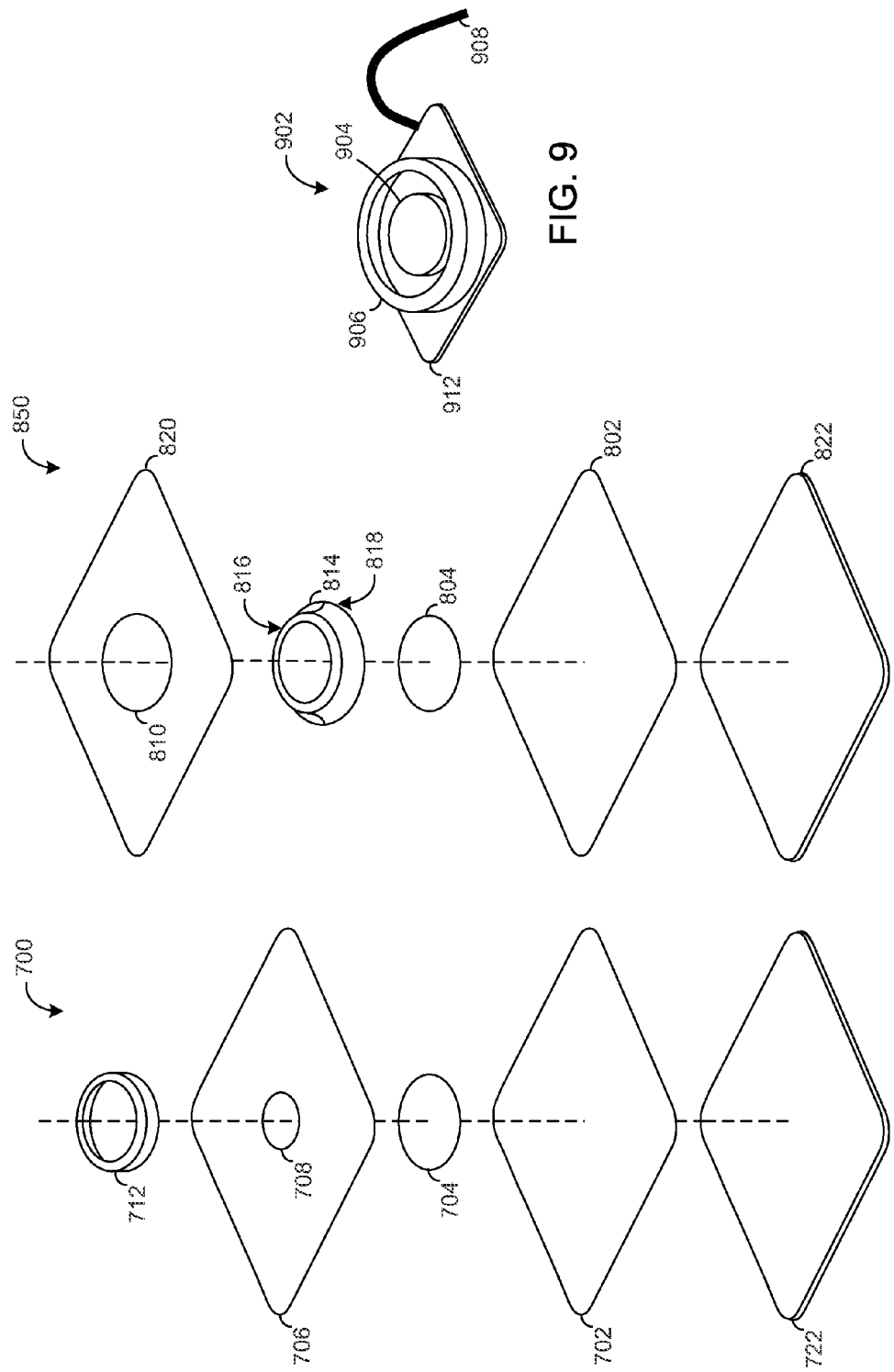

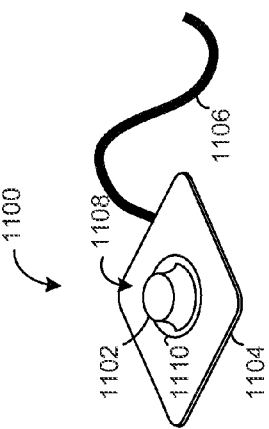
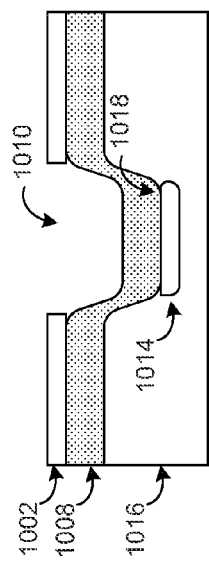
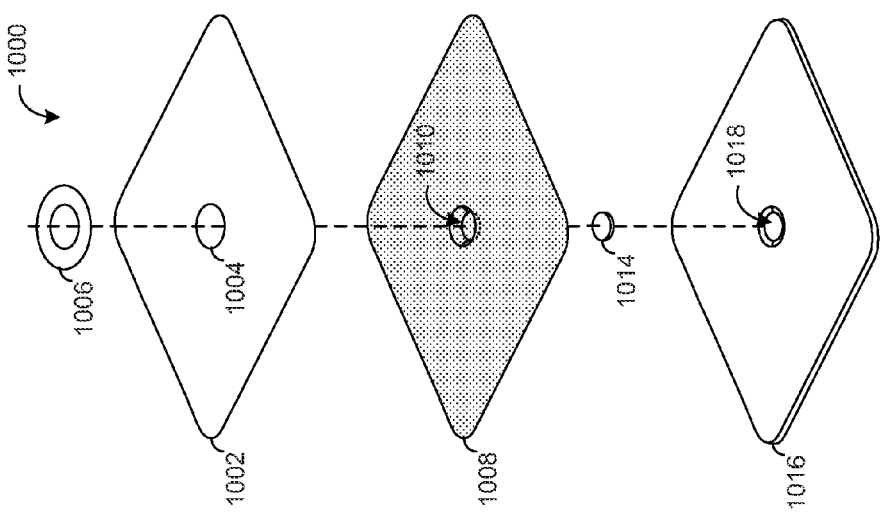

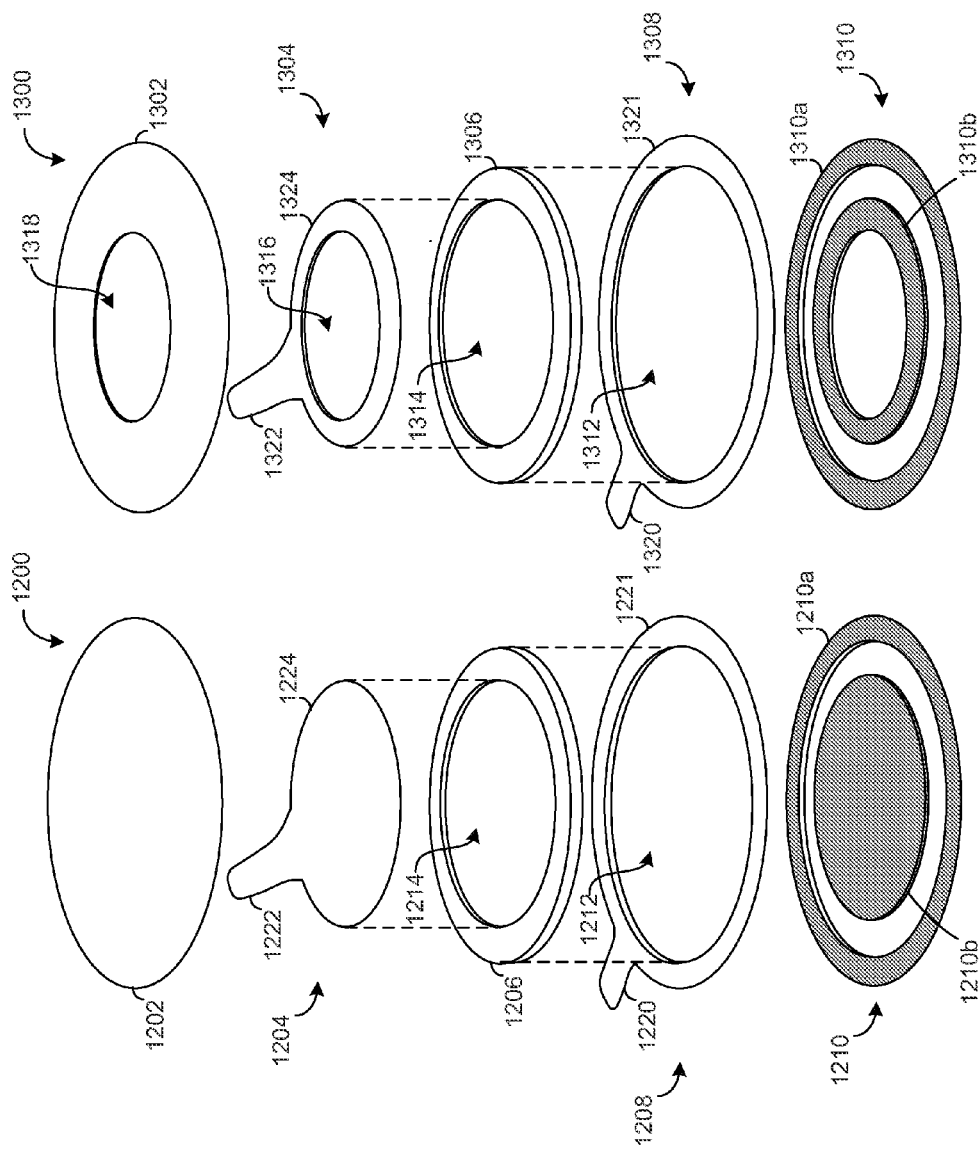

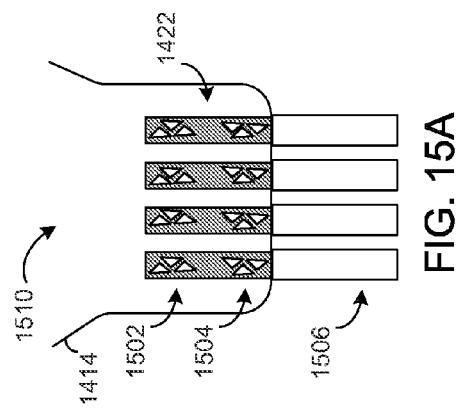
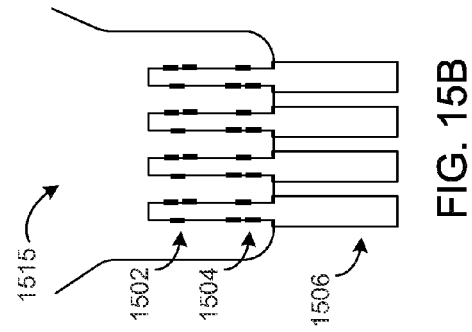
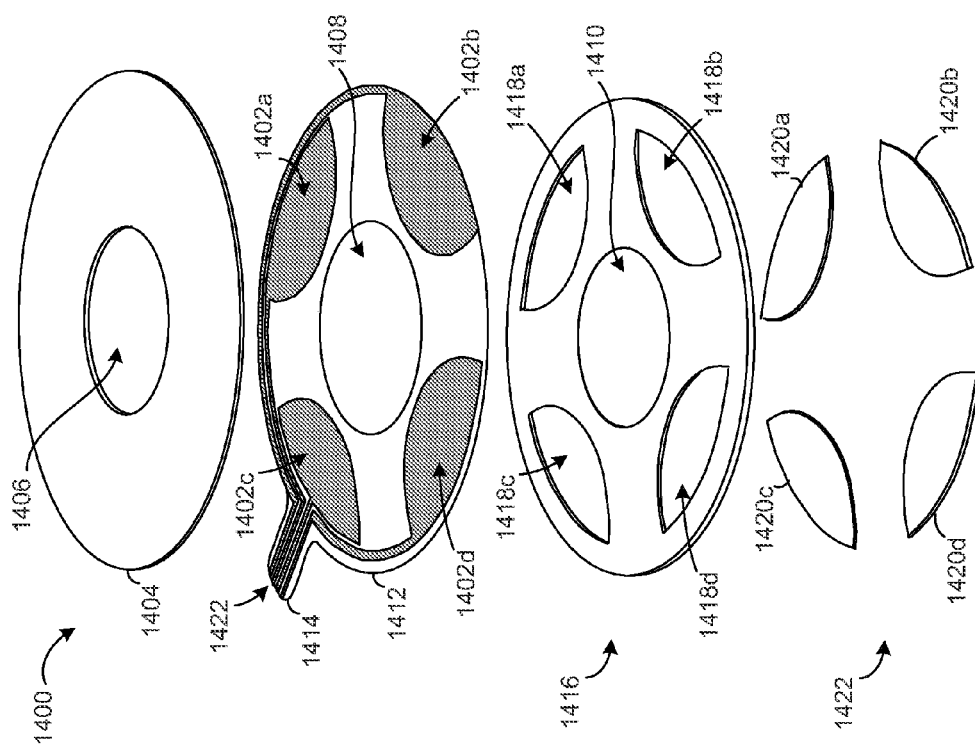

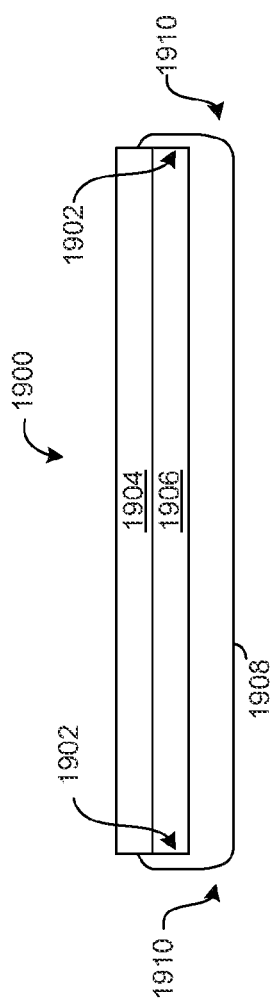
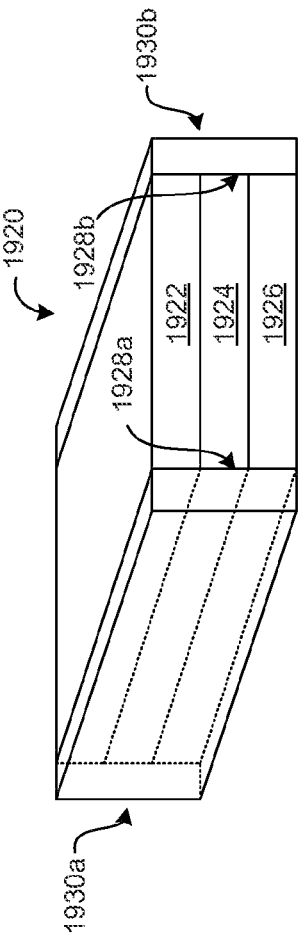
FIG. 19A
FIG. 19B

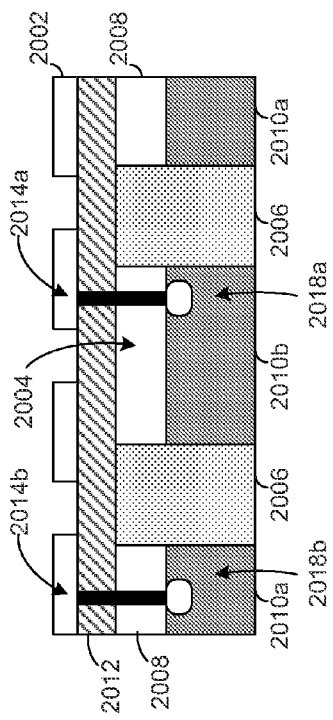
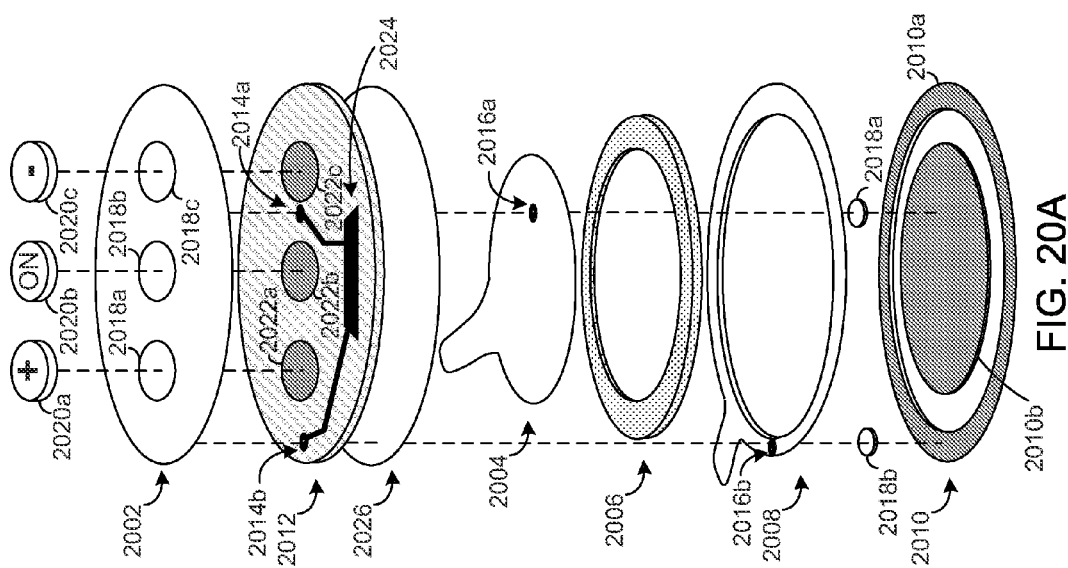
FIG. 20B
FIG. 20A

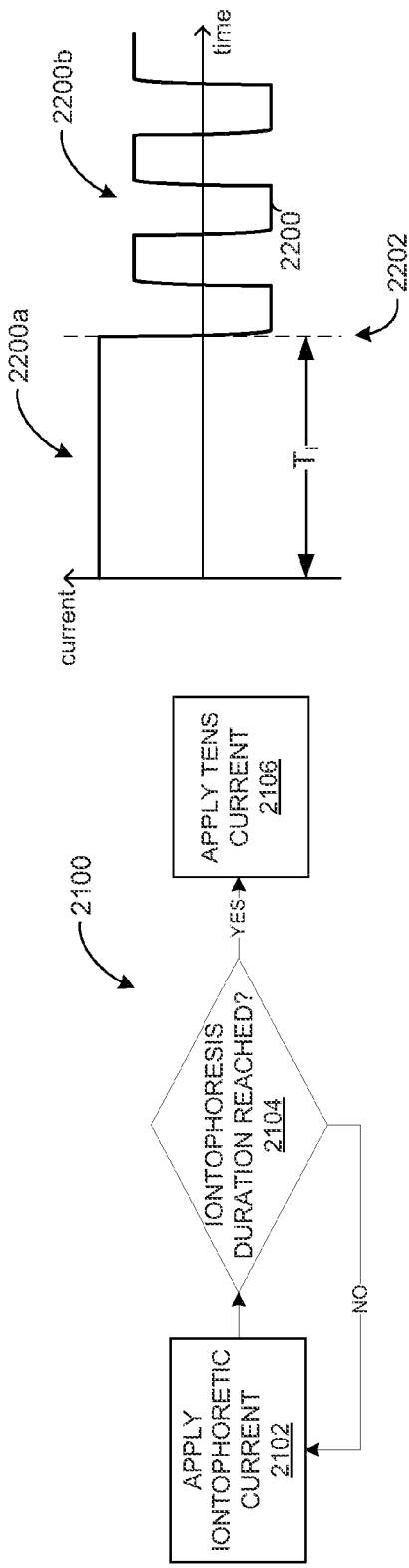
FIG. 21
FIG. 22
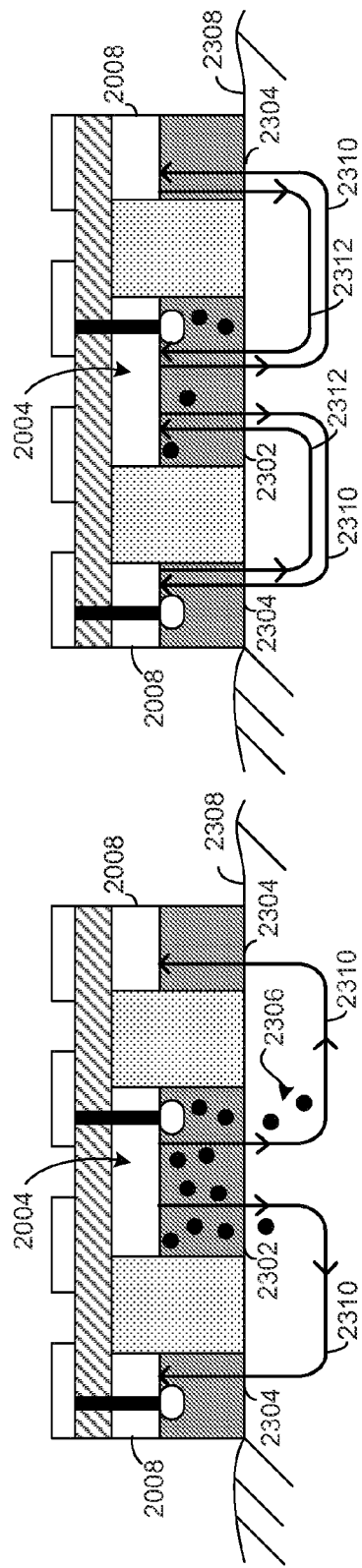
FIG. 23A
FIG. 23B

| FIG. 25-1 | FIG. 25-2 |

| Figure 27-3 |
| Figure 27-2 |
| Figure 27-1 |

ELECTRODES, ELECTRODE SYSTEMS, AND METHODS OF MANUFACTURE

CROSS-REFERENCE TO RELATED APPLICATION

This applications claims priority to U.S. Provisional Patent Application No. 61/508,874, filed Jul. 18, 2011, which is hereby incorporated by reference in its entirety herein.

BACKGROUND

Conventional electrodes for medical use suffer from a number of drawbacks. First, some electrodes are hand-manufactured by manually separating the strands of one end of a multi-strand wire and fanning each of these strands to a conductive polymer impregnated with carbon to form an electrode and a pigtail. A separate connector is then attached to the other end of the multi-strand wire, often by hand-soldering. Using a multi-strand wire as an electrode pigtail results in a number of discrete contact points between the wire and the conductive polymer, each of which may form a "hotspot" that disrupts even current distribution over the surface of the electrode and may burn the patient during electrostimulation therapy. Non-uniformities in the connections between the strands of the wire and the conductive polymer may also increase the risk of hotspots. Such electrodes cannot be cut or readily fabricated in the range of shapes that clinicians and patients would like in order to provide targeted and customized therapy. Some electrodes include snap connectors instead of pigtails, which also suffer from the risk of hotspots and can be difficult to connect and disconnect to an electrostimulation lead.

SUMMARY

Described herein are electrodes, electrode connectors, stimulation systems, and methods of assembling the same. In one aspect, an electrode is provided. In certain implementations, the electrode includes a conductive layer having a first area designed for application of therapeutic electrical stimulation to a patient's tissue and a second area including a tail configured as a unitary extension of the first area. In some implementations, the conductive layer is made of aluminum. A connector is disposed on a distal end of the tail and a nonconductive top layer is disposed along a top portion of the conductive layer. In some implementations, a tip of the distal end of the tail is flared. The flared tip may form a tube with an inner passage configured to receive a male pin. In some implementations, the connector includes a connector housing with an undulating receptacle. The distal end of the tail may connect to a conducting connection portion of the undulating receptacle. In some implementations, the distal end of the tail is crimped or glued to a connector configured to couple with a lead from an electrical stimulation generator.

In some implementations, a second conductive layer is disposed on the distal end of the unitary tail. The second conductive layer and the distal end of the unitary tail may be formed into a tube with an inner passage that is configured to receive a male pin from an electrical stimulation lead. The second conductive layer may be a carbon strip, or a conductive polyvinylchloride or polyurethane impregnated with carbon, for example.

In some implementations, the electrode includes a gel layer disposed beneath the conductive layer. In some implementations, the electrode includes a nonconductive bottom layer disposed along a bottom portion of the tail of the conductive layer. The nonconductive bottom layer may include an extension portion disposed partially beneath the conductive layer. The extension portion of the bottom layer may also be disposed partially beneath a gel layer. In some implementations, the conductive layer has a perimeter side surface and a gel coating disposed at least partially about the perimeter side surface. The gel coating may extend around the entire perimeter of the side surface.

In certain implementations, the electrode includes a nonconductive top layer, a conductive layer disposed beneath the nonconductive top layer, a gel layer disposed beneath the conductive layer; and a snap connector. The snap connector includes a first conductive housing disposed above the nonconductive top layer and a second housing disposed beneath the conductive layer, the second housing being at least partially nonconductive and configured to join the first conductive housing to span the conductive layer and the nonconductive top layer. In some implementations, the second housing includes a second conductive housing disposed between a nonconductive element and the first conductive housing, with the second conductive housing disposed beneath the conductive layer. The nonconductive element may be a polymer. In some implementations, the conductive layer has a perimeter side surface and a gel coating disposed at least partially about the perimeter side surface. The gel coating may extend around the entire perimeter of the side surface.

In certain implementations, the electrode includes a conductive layer, a conductive magnetic layer disposed along a top portion of the conductive layer, a nonconductive top layer disposed along a top portion of the conductive magnetic layer, and a socket disposed along a top portion of the nonconductive top layer and configured to receive a magnetic lead connector. In some implementations, the conductive layer is aluminum. In some implementations, the conductive magnetic layer includes a ferritic material, such as stainless steel. In some implementations, a diameter of the conductive magnetic layer is smaller than a diameter of the conductive layer. In some implementations, the socket has a base portion with a base diameter and a top portion with a top diameter, the base diameter larger than the top diameter. The base portion may be disposed below the nonconductive top layer and the top portion may be disposed above the nonconductive top layer.

In certain implementations, the electrode includes a nonconductive top layer, a conductive layer disposed beneath the nonconductive top layer, a gel layer disposed beneath the conductive layer, and a receptacle structured as a depression in the conductive layer configured to receive a male connector of a lead from an electrostimulation system. A nonconductive element is disposed beneath the receptacle. In some implementations, the receptacle is configured to receive a male snap connector. In some implementations, the nonconductive element is disposed between a bottom surface of the receptacle and a bottom surface of the gel layer.

In another aspect, an electrode system is provided. In certain implementations, the electrode system includes a plurality of conductive zones, each conductive zone including an electrode having a conductive layer with a unitary tail. The electrode system also includes a plurality of connectors, each connector disposed on a distal end of each of the unitary tails, and a nonconductive top layer disposed above the conductive zones. The plurality of conducting zones may be separated laterally by an insulating foam layer. In some implementations, the plurality of conducting zones are disposed symmetrically about a hole in the nonconductive top layer. The plurality of conductive zones may be disposed concentrically about the hole in the nonconductive top layer. In some implementations, a first of the plurality of conductive zones is disposed between a second of the plurality of conductive zones and the nonconductive top layer. A nonconductive layer may also be disposed between the a portion of the first of the plurality of conductive zones and the second of the plurality of conductive zones.

In certain implementations, the electrode system includes an electrode having a socket configured to receive a magnetic lead connector and a lead including a magnetic lead connector, the magnetic lead connector including a magnet configured to seat within the socket. The magnetic lead connector may include an outer wall configured to capture at least a portion of the socket between the outer wall and the magnet.

In some implementations of the electrode and electrode systems described herein, a nonconductive layer is formed in a non-radially symmetric shape. The non-radially symmetric shape may be rectangular. In some implementations of the electrode and electrode systems described herein, a nonconductive layer is formed in an asymmetric shape.

In another aspect, a stimulation system is provided. In certain implementations, the stimulation system includes a nonconductive top layer and an electronics layer, disposed beneath the nonconductive top layer. The electronics layer includes pulse generation circuitry in electrical communication with a first conductive contact point in the electronics layer. The stimulation system also includes a conductive layer, disposed beneath the electronics layer, having a second conductive contact point in electrical contact and alignment with the first conductive contact point via a puncture connection between the electronics layer and the conductive layer. In some implementations, the stimulation system includes a second conductive layer, disposed beneath the electronics layer. The second conductive layer has a third conductive contact point in electrical contact and alignment with a fourth conductive contact point in the electronics layer via a puncture connection between the electronics layer and the second conductive layer. The stimulation system may include any of the electrode or electrode systems described herein.

In another aspect, an iontophoresis delivery system is provided. In certain implementations, the iontophoresis delivery system includes a conductive layer and a drug delivery layer. The drug delivery layer includes a therapeutic compound, and is arranged to deliver the therapeutic compound into a patient's tissue when a DC current is driven into the patient's tissue from the conductive layer. The iontophoresis delivery system also includes an electronics layer comprising pulse generation circuitry. The pulse generation circuitry is configured to deliver the DC current to the conductive layer for a predetermined period of time to drive the therapeutic compound into the patient's tissue, and after delivering the DC current for the predetermined period of time, deliver an AC TENS current to the conductive layer. In some implementations, the iontophoresis delivery system also includes a battery and the pulse generation circuitry is configured to use the battery to power the delivery of the DC current and the delivery of the AC TENS current. In some implementations, the iontophoresis delivery system includes a chemical switch configured to indicate that the predetermined period of time has elapsed when a predetermined amount of therapeutic compound has been driven into the patient's tissue.

In another aspect, a method of assembling an electrode is provided. In certain implementations, the method includes providing a conductive layer having a first area designed for application of therapeutic electrical stimulation to a patient's tissue and a second area including a tail configured as a unitary extension of the first area, disposing a nonconductive top layer along a top portion of the conductive layer, and forming a connector at the distal end of the tail. Forming a connector at the distal end of the tail may include inserting the distal end of the tail into a receptacle and crimping the receptacle to secure the distal end of the tail within the receptacle. The distal end of the tail may include a flared portion with first and second sides, in which case forming a connector may include securing the first and second sides in proximity to one another to form a tube from the flared portion. The securing may include arranging the first and second sides in proximity with one another, disposing a length of heat-shrink tubing around the flared portion when the first and second sides are arranged in proximity, and heating the heat-shrink tubing to reduce the diameter of the heat-shrink tubing around the flared portion, thereby capturing the flared portion in a tubular configuration.

In another aspect, a method of assembling an electrode is provided. In certain implementations, the method includes providing a conductive layer, forming a depression in a top surface of the conductive layer, the depression configured as a receptacle for receiving a male connector of a lead from an electrostimulation system, and disposing a gel layer on a bottom surface of the conductive layer. In some implementations, the method also includes disposing a nonconductive element beneath the depression, between the bottom surface of the conductive layer and a bottom surface of the gel layer.

In another aspect, a method of assembling an electrode system is provided. In certain implementations, the method includes providing a first ring-shaped conductive layer, disposing a ring-shaped conductive layer within an interior of the first ring-shaped conductive layer, disposing a second conductive layer within an interior of the ring-shaped conductive layer, and disposing a nonconductive top layer along a top portion of the first and second ring-shaped conductive layers. The second conductive layer may be ring-shaped.

In another aspect, a method of assembling a stimulation system is provided. In certain implementations, the method includes providing an electronics layer including pulse generation circuitry in electrical communication with a first conductive contact point in the electronics layer, disposing a conductive layer beneath the electronics layer, and puncturing the electronics layer and the conductive layer at the first conductive contact point to form an electrical connection between the conductive contact point of the electronics layer and the conductive layer. In some implementations, the method further includes disposing a gel layer beneath the conductive layer and disposing a nonconductive top layer above the electronics layer. In some implementations, the electronics layer includes one or more switches configured to control the pulse generation circuitry, and the method further includes disposing one or more buttons in alignment with the one or more switches such that pressing the one or more buttons activates the corresponding one or more switches. In some implementations, the one or more switches includes a power-on switch and pressing the button associated with the power-on switch initiates delivery of electrical pulses from the pulse generation circuitry to the conductive layer.

In another aspect, a method of configuring a single device for the delivery of iontophoretic and TENS treatments is provided. In certain implementations, the method includes providing an electrical stimulation system having a conductive layer, a drug delivery layer with a therapeutic compound, and pulse generation circuitry. The method may further include configuring the pulse generation circuitry to, upon activation when positioned on a patient's tissue, deliver a DC current to the conductive layer for a predetermined period of time to drive the therapeutic compound from the drug delivery layer into the patient's tissue and after delivering the DC current for the predetermined period of time, deliver an AC TENS current to the conductive layer. In some implementations, the pulse generation circuitry includes a battery and the method further includes configuring the pulse generation circuitry to use the battery to power the delivery of the DC current and the delivery of the AC TENS current. In some implementations, the method further includes configuring the pulse generation circuitry to deliver the AC TENS current until the battery is depleted.

Variations and modifications will occur to those of skill in the art after reviewing this disclosure, where disclosed features may be implemented in any combination and subcombinations (including multiple dependent combinations and subcombinations), with one or more other features described herein. The various features described or illustrated above, including any components thereof, may be combined or integrated in other systems; moreover, certain features may be omitted or not implemented.

Examples of changes, substitutions and alterations are ascertainable by one skilled in the art and to be made without departing from the scope of the information disclosed herein. All references cited herein are incorporated by reference in their entirety and made part of this application.

BRIEF DESCRIPTION OF THE DRAWINGS

The foregoing and other objects and advantages will be appreciated more fully from the following description, with reference to the accompanying drawings wherein:

FIG. 1A is an exploded view of a unibody electrode;

FIG. 1B is a plan view of certain components of the unibody electrode of FIG. 1A;

FIGS. 4A-4C are perspective views of another connector;

FIGS. 7 and 8 are exploded views of magnetic connector electrodes;

FIG. 9 is a perspective view of a magnetic lead connector;

FIG. 10A is an exploded view of an inverted snap electrode, and FIG. 10B is a cross-sectional view of the inverted snap electrode of FIG. 10A;

FIG. 11 is a perspective view of a connector for an inverted snap electrode;

FIG. 12 is an exploded view of an electrode system;

FIG. 13 is an exploded view of another electrode system;

FIG. 14 is an exploded view of another electrode system;

FIGS. 15A and 15B are front and back plan views, respectively, of a lead connection system;

FIG. 19A is a cross-sectional view of an electrode body;

FIG. 19B is a cross-sectional view of an electrode tail;

FIG. 20A is an exploded view of a stimulation system with an electronics layer, and FIG. 20B is a cross-sectional view of the stimulation system of FIG. 20A;

FIG. 21 is a flow diagram illustrating the operation of a stimulation system configured to deliver iontophoretic and TENS therapy;

FIG. 22 depicts an illustrative waveform that may be generated by a stimulation system configured to provide an iontophoretic treatment followed by a TENS treatment;

FIGS. 23A and 23B are cross-sectional views of a stimulation system applying an iontophoretic treatment and a TENS treatment, respectively;

FIGS. 27-1, 27-2, and 27-3 are an electrical schematic of circuitry that may be used to implement the circuitry of FIG. 26.

DETAILED DESCRIPTION

Figure 2B:
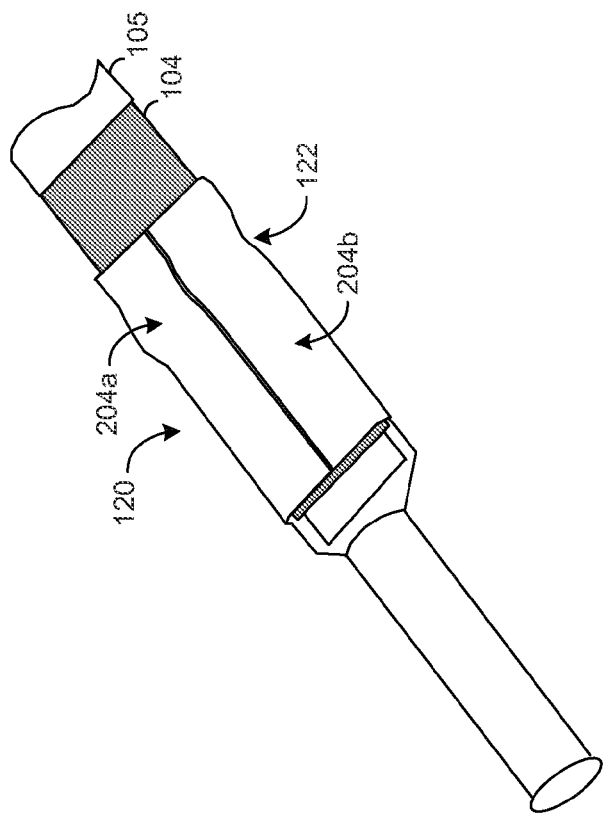
FIGS. 2A and 2B are perspective views of a connector.

FIG. 1A is an exploded view of a unibody electrode 100. The electrode 100 includes a nonconductive top layer 106, a conductive layer 102, a gel layer 118 and a nonconductive bottom layer 112. The conductive layer 102 includes a body 117 and a unitary tail 104 which has a distal end 104a and a proximal end 104b. The proximal end 104b extends into the body 117 and the distal end 104a seats inside an undulating receptacle 122 of a connector housing 120 included in a connector 108. A distal end 128 of the connector housing 120 is configured to couple with a lead from an electrostimulation device (not shown), thereby coupling the conductive layer 102 to the electrostimulation device so that electrostimulation current generated by the electrostimulation device may be applied to a patient's tissue through the electrode 100. The connector 108 also includes a connector jacket 126 which fits over the connector housing 120.

The nonconductive top layer 106 is disposed along a top portion 114 of the conductive layer 102. The nonconductive top layer 106 may be made from a nonconductive sheet material, such as PTE, and includes an adhesive on its bottom surface 107, which is used to adhere the nonconductive top layer 106 to the conductive layer 102. The dimensions of the nonconductive top layer 106 are approximately coextensive with the dimensions of the conductive layer 102, although the tail 105 of the nonconductive top layer 106 may be shorter than the tail 104 of the conductive layer 102 so that when the electrode 100 is assembled, the tail 105 is not interposed between the tail 104 and the undulating receptacle 122 (as shown in FIG. 2B).

The conductive layer 102 and its unitary tail 104 are preferably formed from a continuous piece of aluminum, although any other conductive material, such as another metal or a conductive plastic (e.g., a polymer impregnated with carbon), may be used. The conductive layer 102 and its unitary tail 104 may be formed by die-cutting a sheet of conductive material, for example. Unlike conventional electrodes which have pigtails made of multi-strand wire, the unitary tail 104 is continuous with the body 117 of the conductive layer 102. This construction eliminates irregular connections between the tail 104 and the body 117, which helps distribute the current more evenly about the conductive surface. This even distribution helps prevent the formation of hotspots that can occur at irregularities in a conductive surface and avoid the corrosion that occurs when two dissimilar metals are joined. Additionally, the pull strength of the interface between the unitary tail 104 and the body 117 of the conductive layer 102 need not depend on the quality or uniformity of strand fanning or the adhesion of different layers, resulting in more consistent mechanical properties between electrodes in a given manufacturing batch.

The gel layer 118 is disposed beneath the conductive layer 102. Any of a wide variety of gels, such as conductive hydrogels, may be used in the gel layer 118. However, some conducting materials that may otherwise be desirable in the conductive layer 102, such as aluminum, may not readily adhere to commonly-available gels that may be used in the gel layer 118. If the strength of the adhesion between the conductive layer 102 and the gel layer 118 is not sufficient, the conductive layer 102 may delaminate from the gel layer 118 during use (e.g., when the electrode 100 is peeled from a liner material that protects the gel layer 118 before use, or when the electrode 100 is removed from a patient's tissue). Delamination can be inconvenient for patients and clinicians, often causing uneven contact between the conductive layer 102 and the gel layer 118, resulting in non-uniform current across the patient's tissue during electrostimulation which may burn the patient or fail to stimulate the therapeutically-desired areas. One way to reduce the likelihood of delamination when using an aluminum conductive layer 102 is to change the chemistry of the gel to improve the strength of adhesion between the conductive layer 102 and the gel layer 118. However, the chemical changes that improve the strength of adhesion may also reduce the "legginess" of the gel layer 118 (i.e., the ability of the gel layer 118 to elongate or stretch). Gels with reduced legginess are less conformable to the surface of a patient's tissue (which includes non-uniformities such as skin grooves and underlying bones), resulting in uneven contact between the electrode 100 and the patient's tissue and thus uneven current distribution. Additionally, electrodes that use gels with reduced legginess cannot be reused as often as gels with higher legginess (which are "stickier" and thus more readily and repeatedly adhered to a patient), impeding the repositioning of the electrodes during therapy.

To reduce the likelihood of delamination while still using a sufficiently "leggy" gel layer 118 to facilitate an even current distribution, the nonconductive bottom layer 112 is disposed along a bottom portion 116 of the unitary tail 104 and includes an extension portion 124 that is disposed partially beneath the conductive layer 102 and a portion of its body 117, and partially beneath the gel layer 118. FIG. 1B is a plan view of the relative position of the nonconductive bottom layer 112 and the extension portion 124 with respect to the gel layer 118. When the electrode 100 is removed from a patient's tissue by lifting the electrode tail 126, the extension portion 124 provides a "spatula" effect, lifting the gel layer 118 off the tissue from the bottom of the gel layer 118 and reducing the possibility of delamination between the conductive layer 102 and the gel layer 118. By providing this additional point of leverage for removing the electrode 100 from the patient's tissue, the extension portion 124 allows the electrode 100 to include a wider variety of materials in the gel layer 118, including "leggier" gel materials, with reduced risk of delamination that has inhibited the types of gel materials used in prior electrodes.

The connector 108, which includes the connector housing 120 and the connector jacket 126, provides an electrical interface between a lead from an electrostimulation device (not shown) and the conductive layer 102. The connector housing 120 is made from a conductive material, while the connector jacket 126 is made from an insulating material. In some implementations, the connector jacket 126 is formed from a segment of heat shrink tubing that is positioned over the connector housing 120 and heated to mold to the contours of the connector housing 120. In some implementations, the connector jacket 126 is formed on top of the connector housing 120 by coating the connector housing 120 with a fluid material, such as a silicone or a plastic, which then hardens. The connector jacket 126 may also be formed by wrapping the connector housing 120 with a tape or other material. The connector jacket 126 may be positioned around the connector housing 120 before or after a mechanical crimping operation that forms the shape of the undulating receptacle 122 (as discussed with reference to FIGS. 2A and 2B), and may extend past the end of the undulating receptacle 122. In some implementations, the connector jacket 126 extends past the end of the undulating receptacle 122 and past the distal end 103 of the nonconductive top layer 105 in order to protect the conductive connector housing 120 and any exposed surface of the conductive tail 104 from accidental contact with a patient, clinician, or another electrical device.

Figure 2A:
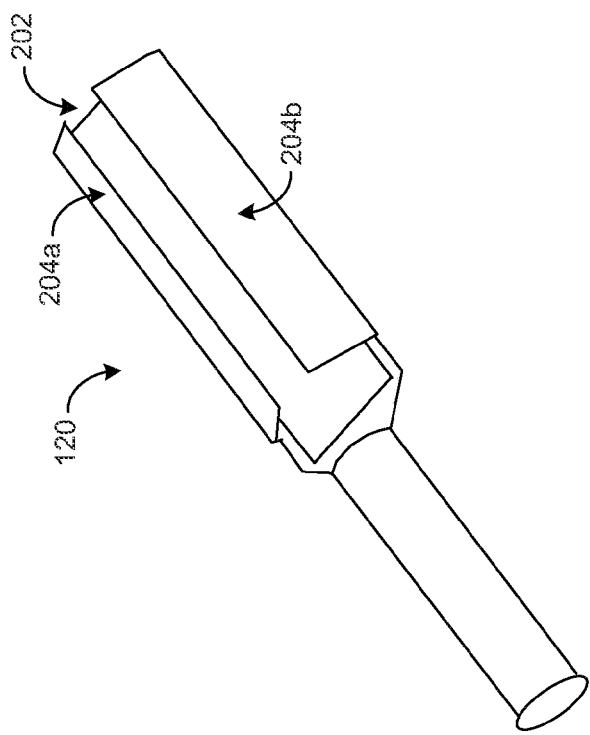
Figures 1, 25:
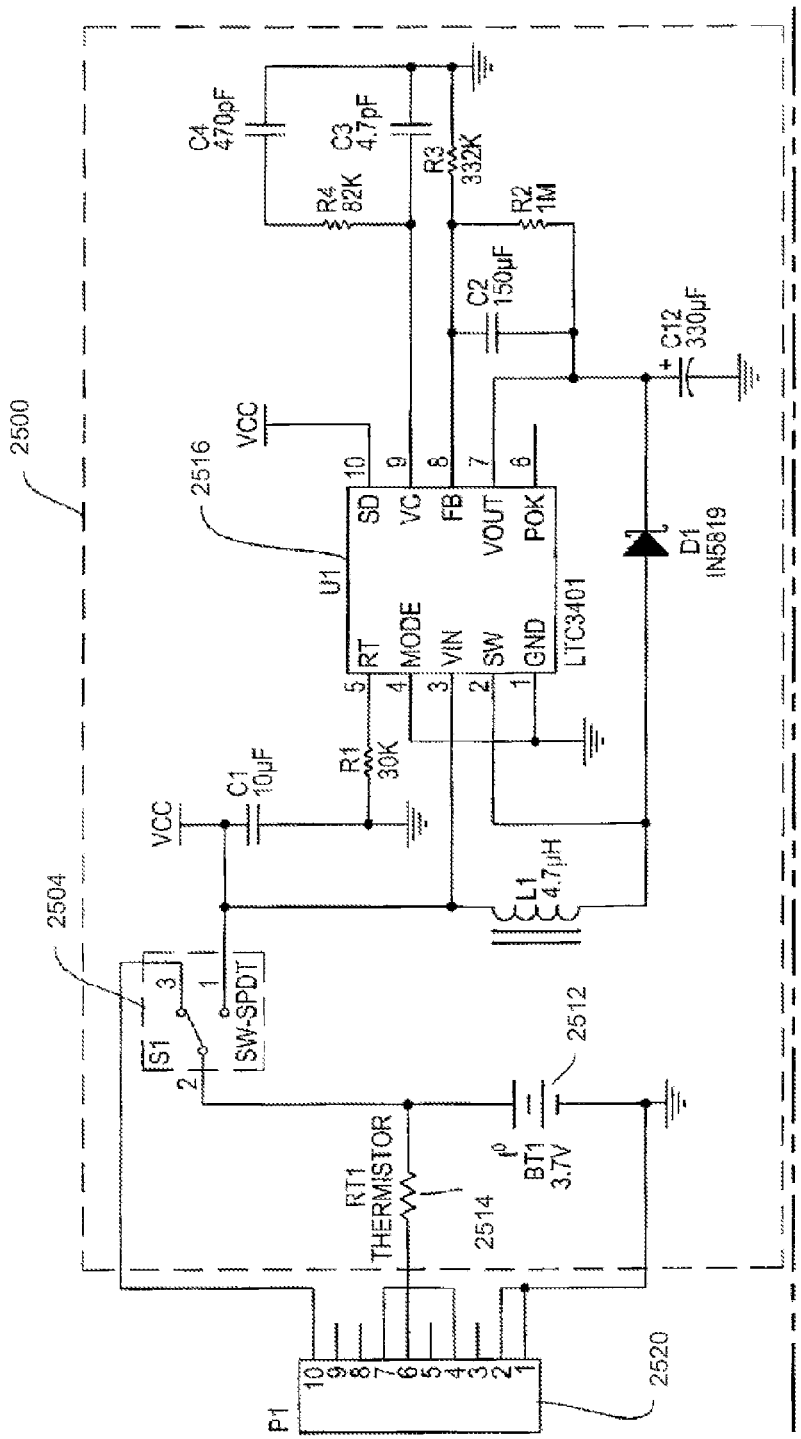
FIGS. 25-1 and 25-2 are an electrical schematic of a circuit that may be used to implement the circuitry of FIG. 24.
Figures 2, 25:
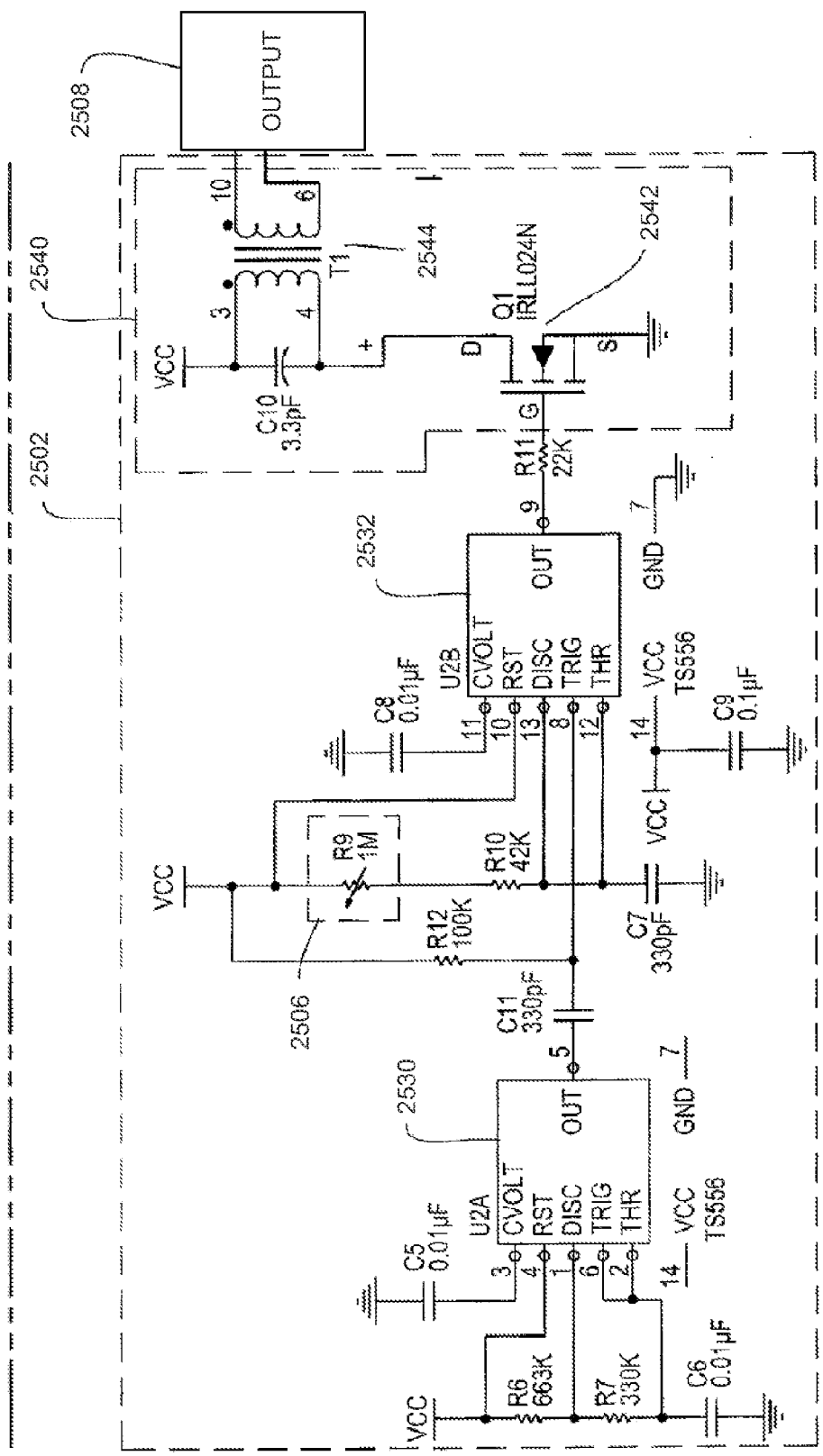

FIGS. 2A and 2B illustrate the connector housing 120 before and after it is mated with the distal end 104a of the unitary tail 104 of FIG. 1. In FIG. 2A, the connector housing 120 includes a conducting connector portion 202 and flaps 204a and 204b. To mate the connector housing 120 with the distal end 104a of the unitary tail 104, the distal end 104a is inserted between the conducting connection portion 202 and the flaps 204a and 204b so that the distal end 104a of the unitary tail 104 is an electrical contact with the conducting connection portion 202. The flaps 204a and 204b are then folded on top of the distal end 104a to mechanically secure the distal end 104a between the flaps 204a and 204b and the conducting connection portion 202. In some implementations the flaps 204a and 204b are also made of a conductive material; in some implementations, the entire connector housing 120 is conductive. After the flaps 204a and 204b have been folded on top of the distal end 104a of the unitary tail 104, the connector housing is crimped to put one or more waves in the connector housing 120, forming an undulating receptacle 122 that contains the distal end 104a of the unitary tail 104. These waves provide additional pull strength which prevents the connector housing 120 from being separated from the unitary tail 104 by a longitudinal force and also improves the electrical connection between the unitary tail 104 and the conducting connection portion 202. An undulating receptacle may include one, two, three, or more waves.

Figure 3:
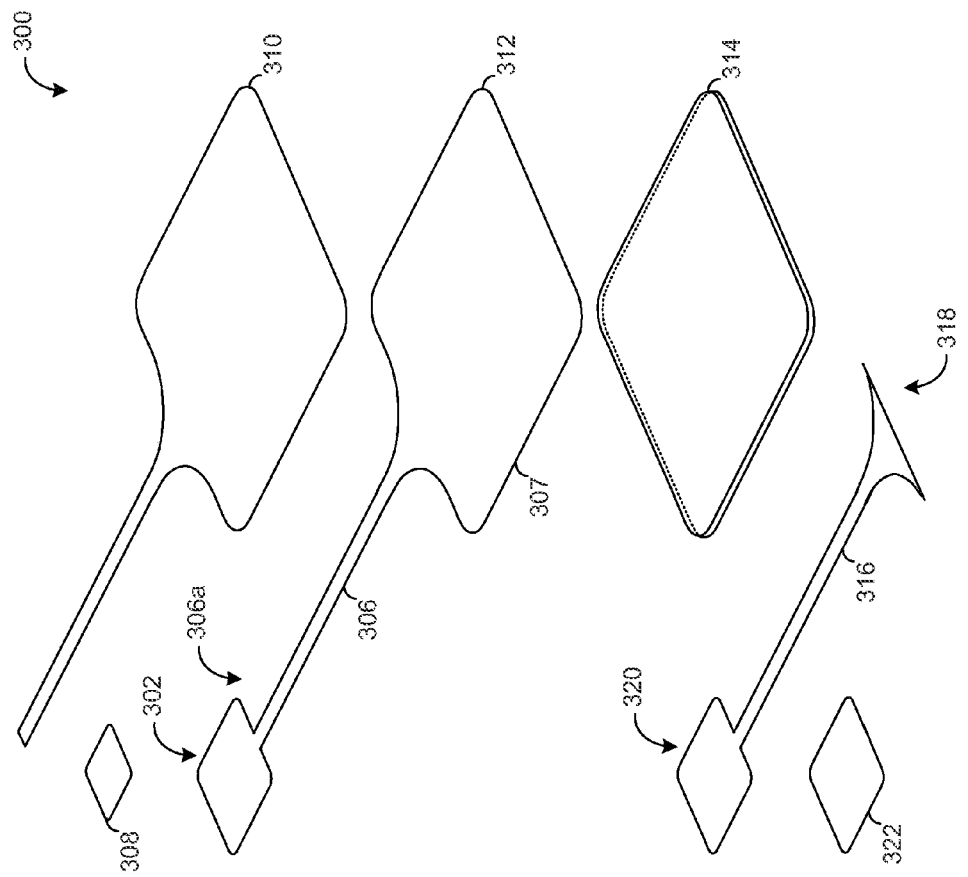
FIG. 3 is an exploded view of another unibody electrode.

FIG. 3 is an exploded view of a unibody electrode 300. The electrode 300 includes a nonconductive top layer 310 disposed along the top of a conductive layer 312 and a gel layer 314 disposed beneath the conductive layer 312. The electrode 300 also includes a nonconductive bottom layer 316 with an extension portion 318 disposed partially beneath the conductive layer 312 and partially beneath the gel layer 314. The materials and arrangements of the nonconductive top layer 310, the conductive layer 312, the gel layer 314, and the nonconductive bottom layer 316 are as described above for the corresponding components of the unibody electrode 100 of FIG. 1. The conductive layer 312 also includes a unitary tail 306 which has at its distal end 306a a flared portion 302. The flared portion 302, the unitary tail 306 and the body 307 of the conductive layer 312 are formed from a continuous conductive material. The nonconductive bottom layer 316 also includes a flared portion 320. The flared portion 320 of the nonconductive bottom layer 316 may have approximately the same dimensions as the flared portion 302 of the unitary tail 306. In some implementations, the conductive layer 312 and the nonconductive bottom layer 316 are die cut to have the same dimensions.

FIG. 3 also illustrates a second conductive layer 308 disposed on the flared portion 302 of the distal end 306a of the unitary tail 306. In some implementations the second conductive layer 308 is formed from a different conductive material than the conductive layer 312. For example, the conductive layer 312 may be formed from aluminum and the second conductive layer 308 may be a carbon strip or a conductive plastic such as a conductive polyvinylchloride or a polyurethane impregnated with carbon. The second conductive layer 308 may provide additional stiffness to the flared portion 302 of the unitary tail 306. In some implementations, the extra stiffening provided by the second conductive layer 308 allows the flared portion 302 to be formed by automated manufacturing equipment (e.g., conversion equipment) into a connector for the electrode 300, and may increase the mechanical strength of the resulting connector. Further description is provided below of representative (non-limiting) implementations connectors formed from the flared portion 302. FIG. 3 also illustrates a bottom support layer 322 which is formed from a nonconductive material and may be included in the electrode 300 instead of or in addition to the flared portion 320 of the nonconductive bottom layer 316 to provide mechanical support.

FIGS. 4A-4C illustrate a connector 400 formed from the electrode 300 illustrated in FIG. 3. FIG. 4A illustrates a nonconductive top layer 404 disposed on top of a conductive layer 406, forming an electrode tail 402 with a flared portion 408 located at its distal end. The flared portion 408 is an extension of the conductive layer 406 and has a second conductive layer 422 disposed thereon. The sides 420a and 420b of the flared portion 408 are curved toward one another, for example, using a mandrel or another suitable manufacturing process. FIG. 4B illustrates the tube 410 that is formed when the sides 420a and 420b are brought together. The sides 420a and 420b may be attached to one another by sealing, gluing, stapling, or may simply be overlapped. FIG. 4B also illustrates a segment of heat-shrink tubing 414. Once the sides 420a and 420b have been brought into proximity, the heat-shrink tubing 414 is positioned over the tube 410, extending onto the unitary tail 406 beyond the tube 410. When heat is applied, the heat-shrink tubing 414 will preferably conform to the unitary tail 406 and to the tube 410, as shown in FIG. 4C. Once the heat-shrink tubing 414 has conformed to the tube 410, the heat-shrink tubing 414 provides mechanical support for the tube 410 and the unitary tail 406 and provides electrical insulation between the tube 410 and a user of the electrode. The tube 410 forms an inner passageway 412 which is configured to receive a male pin from an electrostimulation lead (not shown). The second conductive layer 422 on the flared portion 408 helps strengthen the connector 400 against the wear and tear of to connection and disconnection. The process of forming the connector 400 from the flared portion 408 of the unitary tail of the conductive layer 406 may be automated, further improving the uniformity of the electrodes.

Figure 5:
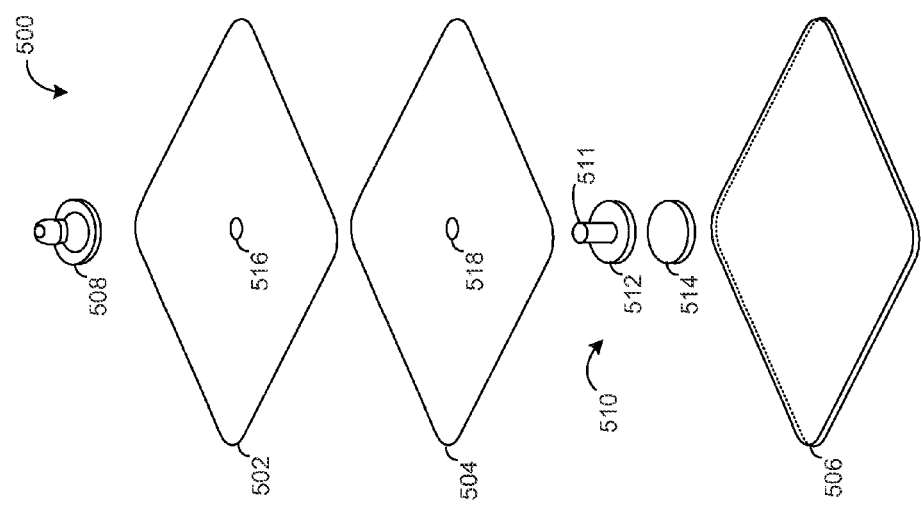

FIG. 5 is an exploded view of a snap electrode 500. The electrode 500 includes a nonconductive top layer 502 with a first aperture 516, a conductive layer 504 with a second aperture 518, and a gel layer 506. The materials and arrangements of the nonconductive top layer 502, the conductive layer 504, and the gel layer 506 are as described above for the corresponding components of the unibody electrodes 100 and 300 of FIGS. 1 and 3, respectively. The snap electrode 500 further includes a first conductive housing 508 and a second housing 510 with a conductive post 511 that is anchored to the second housing 512 and fits within a receptacle (not shown) of the first conductive housing 508 to join the two housings 508 and 510. The second housing 510 includes a second conductive housing 512 disposed beneath the conductive layer 504. The second conductive housing 510 also includes a nonconductive element 514 disposed beneath the second conductive housing 512 and the conductive layer 504 and above the gel layer 506. The second aperture 518 is sized to receive a portion of the second conductive housing 510. When the snap electrode 500 is assembled, the second housing 510 mates with the first conductive housing 508 to sandwich the conductive layer 504 and the nonconductive top layer 502 with the post 511 extending through the apertures 516 and 518 in the layers 502 and 504, respectively.

The nonconductive element 514 is formed from an insulating material, such as a dielectric polymer, and has perimeter dimensions that are equal to or greater than the footprint of the second conductive housing 512. In use, current from an electrostimulation device passes from an electrical lead (not shown) to the first conductive housing 508, the conductive layer 504, and the second conductive housing 512. The current is then distributed to a patient's tissue through the gel layer 506. The nonconductive element 514 forces current to flow through the gel layer 506 around the nonconductive element 514, preventing excessive current from taking the path of least resistance from the second conductive housing 512 through the portion of the gel layer 506 directly beneath the second conductive housing 512 to the patient's tissue, and thereby preventing a buildup of heat and current (a "hotspot") directly below the first conductive housing 508 and the second conductive housing 512a. Conventional snap electrodes, which do not include a nonconductive element between a conductive layer and a gel layer, tend to form hotspots beneath the snap connector because of such direct current flow, which may burn a patient's tissue. The electrode 500 reduces the likelihood of such hotspots by positioning a nonconductive barrier within a path from the second conductive housing 512 to the patient's tissue, resulting in a more uniform current distribution over the gel layer 506.

Figure 6:
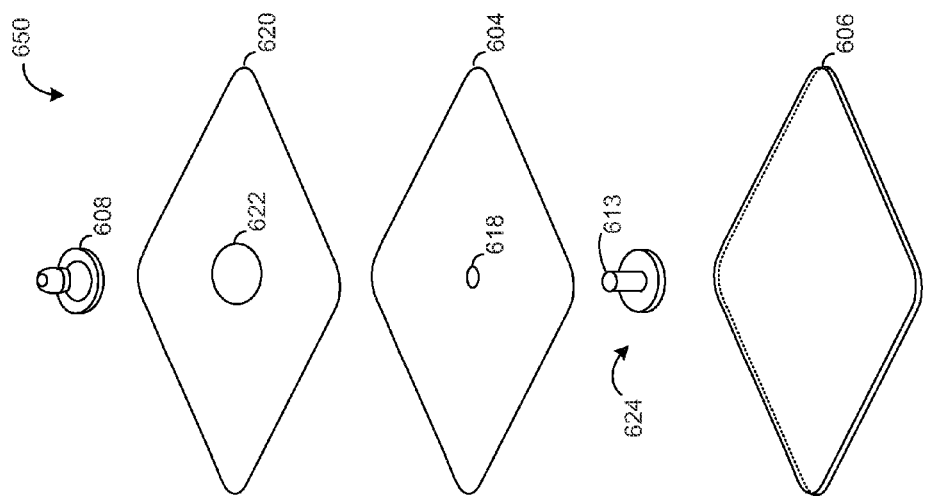
FIGS. 5 and 6 are exploded views of snap electrodes.

FIG. 6 is an exploded view of a snap electrode 650, having a nonconductive top layer 620 with a first aperture 622, a conductive layer 604 with a second aperture 618, and a gel layer 606. The materials and arrangements of the nonconductive top layer 620, the conductive layer 604, and the gel layer 606 are as described above for the electrodes illustrated in FIGS. 1, 3 and 5. The snap electrode 650 further includes a first conductive housing 608 and a second housing 624. The second aperture 618 is sized to receive a post portion 613 of the second housing 624. When the snap electrode 650 is assembled, the port portion 613 of the second housing 624 mates with the first conductive housing 608 to span the conductive layer 604 and the nonconductive top layer 620, as described above with reference to the electrode 500 of FIG. 5. The first conductive housing 608 makes electrical contact with the conductive layer 604 through the aperture 622 in the nonconductive top layer 620.

The second housing 624 is formed from an electrically insulating material, such as a dielectric polymer. Like the snap electrode 500 of FIG. 5, the snap electrode 650 also prevents the formation of a hotspot directly beneath the first conductive housing 608. In use, the nonconductive second housing 624 acts as a barrier to the direct flow of current from the first conductive housing 608 to the patient's tissue through the gel layer 606. The result is a more uniform current distribution over the gel layer 606 and a reduced likelihood of dangerous hotspots.

FIGS. 7 and 8 illustrate magnetic connector electrodes. FIG. 7 is an exploded view of a magnetic connector electrode 700. The electrode 700 includes a socket 712, a nonconductive top layer 706 with an aperture 708, a conductive magnetic layer 704, a conductive layer 702 and a gel layer 722. The materials and arrangements of the nonconductive top layer 706, the conductive layer 702, and the gel layer 722 are as described above for the electrodes illustrated in FIGS. 1, 3, 5 and 6. The socket 712 is formed from a rigid nonconductive material such as a plastic and may be bonded, glued or otherwise affixed to the top of the nonconductive top layer 706. The conductive magnetic layer 704 is positioned below the aperture 708 of the nonconductive top layer 706. The conductive magnetic layer 704 may be formed from a ferritic material, such as a stainless steel, but may be any conductive magnetic material. The conductive layer 702 may be formed from any conductive material such as aluminum. The conductive magnetic layer 704 is positioned between the nonconductive top layer 706 and the conductive layer 702. An adhesive on the bottom surface of the nonconductive top layer 706 sandwiches the conductive magnetic layer 704 between the nonconductive top layer 706 and the conductive layer 702 thereby holding the conductive magnetic layer 704 in place when the magnetic connector electrode 700 is assembled.

FIG. 8 is an exploded view of a magnetic connector electrode 850. The electrode 850 includes a nonconductive top layer 820, with an aperture 810, a socket 814, a conductive magnetic layer 804, a conductive layer 802 and a gel layer 822. Unlike the magnetic connector electrode 700 of FIG. 7, the magnetic connector electrode 850 of FIG. 8 has the socket 814 positioned below the nonconductive top layer 820. The particular implementation of the socket 814 shown in FIG. 8 has a top portion 816 and a bottom portion 818 wherein the diameter of the top portion 816 is smaller than the diameter of the bottom portion 818 and the sides of the socket 814 flare between the top portion 816 and the bottom portion 818. When the electrode 850 is assembled, the top portion 816 of the socket 814 protrudes through the aperture 810 in the nonconductive top layer 820 while the bottom portion 818 of the socket 814 remains below the nonconductive top layer 820. The conductive magnetic layer 804 is disposed under the socket 814. Both the socket 814 and the conductive magnetic layer 804 are sandwiched between the nonconductive top layer 820 and the conductive layer 802, for example, using an adhesive bond between the nonconductive top layer 820 and the conductive layer 802.

The magnetic connector electrodes of FIGS. 7 and 8 provide one or more of a number of advantageous features. First, the use of a magnetic connection mechanism achieves smoother vertical connection and disconnection compared to snap connection mechanisms which require the patient or clinician to overcome a resistive mechanical force in order to connect or disconnect an electrode. This makes it easier for arthritic or impaired users to connect and disconnect the electrodes and also avoids applying a jarring force to damaged or sensitive tissue. Second, because the conductive magnetic layer (layer 704 of FIG. 7 and layer 804 of FIG. 8) is attracted to the magnet included in a magnetic lead connector (such as the magnetic lead connector 904 of FIG. 9), the magnetic connector electrodes of FIGS. 7 and 8 are easier for users to apply and connect in places on the body that are difficult to see, such as the back. Third, the sockets 712 and 814 help a patient or clinician position a magnetic lead connector (such as the magnetic lead connector 902 depicted in FIG. 9) so that the magnetic lead connector is aligned with the conductive magnetic layer (layer 704 of FIG. 7 and layer 804 of FIG. 8) to achieve magnetic coupling sufficient to hold the magnetic lead connector to the electrode. In some implementations, the shape of the socket (such as socket 712 or 814) may be selected so that only magnetic lead connectors of a complementary shape can be seated within the socket (referred to as "keying" the connector to the socket). Keying of the socket and connector allows manufacturers to create magnetic lead connector/electrode combinations that are designed to work together and prevents the use of other magnetic lead connector/electrode combinations that may not be as therapeutically beneficial. Fourth, the sockets 712 and 814 provide a mechanical barrier that prevents a magnetic lead connector from being disconnected from the electrode by a lateral force (such as a tug on the lead wire 908 shown in FIG. 9). Clinically, lateral pulls account for a significant percentage of disconnection events; since the magnetic force between the conductive magnetic layer (layer 704 of FIG. 7 and layer 804 of FIG. 8) and a magnet included in a magnetic lead connector is weaker in the lateral direction than in the vertical direction, the sockets 712 and 814 provide additional security against such pulls.

FIG. 9 illustrates a magnetic lead connector 902 that may be used to mate a lead wire 908 from an electrostimulation device (not shown) to either of the magnetic connector electrodes of FIGS. 7 and 8. The magnetic lead connector 902 includes a connector base portion 912 upon which a magnet 904 is mounted. The magnet 904 is made from a conductive material, such as neodymium, and is electrically connected to the lead wire 908. In some implementations, the magnet 904 is soldered to the lead wire 908 or an intermediate conducting element (not shown); in such implementations, the magnet 904 is preferably kept cool to avoid changing the crystalline structure of the magnet 904 and affecting its magnetic properties. In some implementations, the magnet 904 is held to the connector base portion 912 using a metal claw system that includes a formed female receiver that friction fits with the magnet 904. In some implementations, a glue (such as a conductive glue) may be used to attach the magnet 904 to the connector base portion 912. The magnetic lead connector 902 of FIG. 9 also includes an outer wall 906 which may be formed from a nonconductive material and may be configured to surround a socket of an electrode (such as the socket 712 of FIG. 7 or the top portion 816 of the socket 814 of FIG. 8 when the magnetic lead connector 902 is mated to the electrodes illustrated in the respective figures). The outer wall 906 may provide additional pull strength that prevents the magnetic lead connector 902 from being displaced from connection with either a magnetic connector electrode by a laterally applied force, such as a lateral tug on the lead wire 908. In some implementations of the magnetic lead connector 902, no outer wall is included. When the magnetic lead connector 902 is attached to the electrode 700 of FIG. 7 or the electrode 850 of FIG. 8, the magnet 904 seats within the socket 712 or 814, respectively, and provides an electrical connection between the magnet 904 and conductive magnetic layer (layer 704 of FIG. 7 and layer 804 of FIG. 8). In use, electrostimulation current passes from an electrostimulation current generator (not shown) through the lead wire 908, through the magnet 904, through the conductive magnetic layer, to the conductive layer (layer 702 of FIG. 7 and layer 802 of FIG. 8), and through the gel layer (layer 722 of FIG. 7 and layer 822 of FIG. 8) to a patient's tissue.

FIGS. 10A and 10B illustrate an inverted snap electrode 1000 which may be formed in accordance with the unibody electrode construction techniques described herein. FIG. 10A is an exploded view of the inverted snap electrode 1000. The inverted snap electrode 1000 includes a nonconductive top layer 1002 with an aperture 1004 encircled by a reinforcing ring 1006 disposed above or within the nonconductive top layer 1002. The reinforcing ring 1006 is comprised of a nonconductive material (e.g., any of the materials described herein as suitable for use in a nonconductive or insulating layer), and may provide mechanical reinforcement to the inverted snap electrode 1000 when a snap connector is connected and disconnected from the inverted snap electrode 1000 during use. The inverted snap electrode also includes a conductive layer 1008 with a depression 1010, and a gel layer 1016 with a depression 1018. The materials of the nonconductive top layer 1002, the conductive layer 1008, and the gel layer 1016 are as described above for the corresponding components of the unibody electrodes 100 and 300 of FIGS. 1 and 3, respectively. A nonconductive element 1014 is positioned between the depression 1010 of the conductive layer 1008 and the depression 1018 of the gel layer 1016. FIG. 10B is a cross-sectional view of the inverted snap electrode of FIG. 10A, including the nonconductive top layer 1002, the conductive layer 1008 and the depression 1010, the gel layer 1016 and the depression 1018, and the nonconductive element 1014.

The depression 1010 of the conductive layer 1008 may be mechanically formed in any of a number of ways, such as vacuum forming or thermoforming during a roll manufacturing process. The depression 1010 is formed as a female receptacle to receive a male connector (e.g., the male portion 1102 of the connector 1100 of FIG. 11, described in detail below) within the conductive layer 1008. In some implementations, the depression 1010 is dimensioned to snugly receive a standard male snap connector. In some implementations, the depression 1010 is dimensioned to snugly receive a custom-sized or custom-shaped male connector. A custom male connector may have any depth, width, length or shape, and may act as a "keyed" connector in that only connectors whose shape is complementary to the receptacle formed by the depression 1010 can securely mate with the inverted snap electrode 1000. The use of a keyed connector with the inverted snap electrode 1000 (or any of the electrodes and electrode systems described herein) may improve therapeutic outcomes by reducing the likelihood that the wrong electrode (of a family of keyed electrodes) will be used with a given electrotherapy device or that low-quality electrodes manufactured without approval of the electrotherapy device manufacturer can successfully mate with the keyed connector.

During certain modes of assembly, the nonconductive element 1014 is positioned beneath the bottom surface of the depression 1010 of the conductive layer 1008, between the conductive layer 1008 and the gel layer 1016. The depression 1018 of the gel layer 1016 is complementary to the profile of the depression 1010 and the nonconductive element 1014, but preferably does not extend past the bottom surface of the gel layer 1016 so that a flat gel surface may be applied to the patient's tissue. In a preferred implementation, the gel layer 1016 is poured onto the conductive layer 1008 after the depression 1010 has already been formed and the nonconductive element 1014 positioned, after which the gel layer 1016 is cross-linked in place (referred to as a "pour-in-place" process). The gel layer 1016 and its depression 1018 could also be formed in a mold, either individually or in sheets. As discussed above with reference to the nonconductive element 514 of FIG. 5, the nonconductive element 1014 forces current to flow through the gel layer 1016 around the nonconductive element 1014, preventing excessive current from taking the path of least resistance from the depression 1010 of the conductive layer 1008 through the portion of the gel layer 1016 directly beneath the depression 1010 to the patient's tissue, and thereby preventing a "hotspot" from forming below the depression 1010.

The inverted snap electrode 1000 may have advantages over standard snap electrodes. First, by including a female receptacle within the electrode itself (instead of in the connector, as is typical in snap-electrode-based systems), and thereby lodging in the depth of the male connector within the thickness of the electrode (rather than above the surface of the electrode as in most available systems), the inverted snap electrode 1000 provides a lower profile than existing snap electrode systems. This lower profile allows the inverted snap electrode 1000 to be used in therapeutic settings in which existing snap electrodes are unsuitable, such as within a cast or brace. The low profile of the inverted snap electrode 1000 also reduces the likelihood that the electrode or connector will catch on a patient's clothing or other objects as the patient is moving, and thus may be better suited for electrostimulation or monitoring of active patients (e.g., during sports therapy) than existing electrodes. The inverted snap electrode 1000 may also be easier to use than traditional "low profile" electrodes in which a small lead pin must be fed into a socket at the end of the electrode's lead wire. This may particularly benefit older patients, who typically find snap electrodes easier to use than the lead pin embodiments. Additionally, manufacturing advantages may be achieved by using a roll material (such as an aluminum laminate) to form the conductive layer 1008, or by using a pour-in-place process for adding the gel layer 1016. In some implementations, the inverted snap electrode 1000 may be manufactured using automated conversion equipment, which may result in improved efficiency, reliability and uniformity as compared to electrodes assembled by hand or by machines in which material must be manually transferred and loaded at multiple stages during manufacturing.

FIG. 11 is a perspective view of a connector 1100 that is configured to mate a lead wire 1106 with an inverted snap electrode such as the inverted snap electrode 1000 of FIG. 10. The connector 100 includes a connector base portion 1104 upon which a male portion 1102 is disposed. The male portion 1102 is made from a conductive material and is electrically connected to the lead wire 1106. In some implementations, the male portion 1102 is formed using a same or similar manufacturing technique as discussed above to form the depression 1010 in the conductive layer 1008 of the inverted snap electrode 1000 (e.g., vacuum or thermoforming), and may be formed from the same or a similar material as the conductive layer 1008. As shown, the male portion 1102 extends from the connector base portion 1104 through an aperture 1110 in a nonconductive top layer 1108. The surface of the nonconductive top layer 1108 that faces the connector base portion 1104 may be adhesive, and may mechanically capture the male portion 1102 between the nonconductive top layer 1108 and the connector base portion. In some implementations, no nonconductive top layer 1108 is included in the connector for the inverted snap electrode 1000, and the male portion 1102 is fastened to the connector base portion 1104 using an adhesive, tabs, or other fastener. When the lead connector 1100 is attached to the inverted snap electrode 1000 of FIG. 10, the male portion 1102 seats within the receptacle formed by the depression 1010 and provides an electrical connection between the lead wire 1106 and the conductive layer 1108. In use, electrostimulation current passes from an electrostimulation current generator (not shown), through the lead wire 1106, to the conductive layer 1108, and then to a patient's tissue. As discussed above with reference to FIG. 10, when the connector 1100 is mated with the inverted snap electrode 1000, the two together may have a lower profile than existing snap electrode-connector assemblies, which may result in improved performance and wider use in different therapeutic and diagnostic environments.

Additional variations in electrode design are possible. For example, FIG. 12 is an exploded view of an electrode system 1200 that includes a plurality of electrode structures, similar to the unitary body and tail structures described above. The electrode system 1200 includes a nonconductive top layer 1202, a first electrode 1204, an insulating layer 1206, a second electrode 1208 and a gel layer 1210. The first electrode 1204 and the second electrode 1208 are constructed from a unitary conductive material, as discussed above with reference to FIGS. 1 and 3. The first electrode 1204 includes a unitary tail 1222 and a body 1224. The insulating layer 1206 includes a hole 1214 that is sized to approximately match the outer diameter of the body 1224 of the first electrode 1204. The second electrode 1208 includes a unitary tail 1220 and a body 1221. The body 1221 of the second electrode 1208 includes a hole 1212 sized to approximately match the outer dimensions of the insulating layer 1206. The gel layer 1210 includes a first gel segment 1210a and a second gel segment 1210b. The first gel segment 1210a is sized to approximately match the dimensions of the body 1221 of the second electrode 1208 and the second gel segment 1210b is sized to approximately match the dimensions of the body 1224 of the first electrode 1204. The nonconductive top layer 1202 may have outer dimensions that approximately match the outer dimension of the body 1221 of the second electrode 1208. The bottom surface of the nonconductive top layer 1202 may be coated with an adhesive to which the first electrode 1204, the insulating layer 1206 and the second electrode 1208 may be affixed. When these components are affixed to the nonconductive top layer 1202, the thickness of the insulating layer 1206 may extend below a bottom surface of the second electrode 1208, such that when the first gel segment 1210a and the second gel segment 1210b are affixed to the bottom of the assembly, the bottom of the insulating layer 1206 may be in approximately the same plane as the bottom of the gel layer 1210, thereby presenting a substantially uniform surface to be affixed to the tissue of a patient.

FIG. 13 is an exploded view of an electrode system 1300 constructed in accordance with the description of the electrode system 1200 of FIG. 12. The electrode system 1300 includes a nonconductive top layer 1302, a first electrode 1304, an insulating layer 1306, a second electrode 1308 and a gel layer 1310. The first electrode 1304 and the second electrode 1308 are constructed from a unitary conductive material, as discussed above with reference to FIGS. 1, 3 and 12. The first electrode 1304 includes a unitary tail 1322, a body 1324, and a hole 1316. The insulating layer 1306 includes a hole 1314 that is sized to approximately match the outer dimensions of the body 1324 of the first electrode 1304. The second electrode 1308 includes a unitary tail 1320 and a body 1321 with a hole 1312 that is sized to approximately match the outer dimensions of the insulating layer 1306. The gel layer 1310 includes a first gel segment 1310a and a second gel segment 1310b. The dimensions of the gel segment 1310a are sized to approximately match the dimensions of the body 1321 of the second electrode 1308 and the dimensions of the gel segment 1310b are sized to approximately match the dimensions of the body 1324 of the first electrode 1304.

FIG. 14 is an exploded view of an electrode system 1400. The electrode system 1400 includes a nonconductive top layer 1404 with a hole 1406. The electrode system 1400 further includes a plurality of conductive zones 1402a, 1402b, 1402c and 1402d mounted or printed on a substrate 1412. The substrate 1412 includes a tail portion 1414 with conductive traces 1422 to each of the conductive zones 1402. The substrate 1412 further includes a hole 1408. The electrode system 1400 also includes an insulating layer 1416 that has a plurality of apertures 1418a, 1418b, 1418c and 1418d. Each of the apertures 1418 is positioned to align with a respective conductive zone 1402. The insulating layer 1416 further includes a hole 1410 that is coaxially aligned with the hole 1408 and the hole 1406. The electrode system 1400 also includes a gel layer 1422 which has a plurality of gel segments 1420a, 1420b, 1420c and 1420d. When the electrode system 1400 is assembled, each of the gel segments 1420 is positioned within the respective apertures 1418 of the insulating layer 1416. When the electrode system 1400 is in use, the gel segments 1420 are interposed between the conductive zones 1402 and the patient's tissue.

The electrode system 1400 is compatible with two-channel interferential electrostimulation and TENS therapy, among others. The hole in the center of the electrode system 1400 provides a working area for clinicians who would like to anesthetize a patient's tissue in preparation for or during another medical procedure, such as suturing or a needle stick for drug delivery or testing. The hole also makes it easier to position properly the electrode on a patient's tissue: the patient or clinician can "center" the hole over the site of the patient's pain without having to separately position each conductive zone separately. Additionally, the ease of use of the electrode system 1400 provides an advantageous way to demonstrate the therapeutic effects of electrotherapy to patients who may benefit from its use: the electrode system 1400 and electrostimulation can be applied to a patient's tissue quickly, resulting in a demonstrable effect within a matter of seconds.

FIGS. 15A and 15B are front and back plan views, respectively, of a connection system that may be used to electrically connect conductive traces on an electrode tail (such as the conductive traces 1422 on the tail 1414 of the electrode system 1400 of FIG. 14) to separate connecting elements. In FIG. 15A, the tail 1414 is shown with four conductive portions 1422. Each of these conductive portions is pierced by a set of first teeth 1502 and a set of second teeth 1504 with the first and second teeth mounted respectively on a plurality of connectors 1506. The connectors 1506, including the first and second teeth 1502 and 1506 are formed from a conductive material, and can be attached to wire or other conducting leads to electrically connect an electrode system (such as the electrode system 1400 of FIG. 14) to an electrostimulation device (not shown). FIG. 15B is a back view of the tail 1414 with the connectors 1506 attached to the conductive portions 1422.

Figure 16:
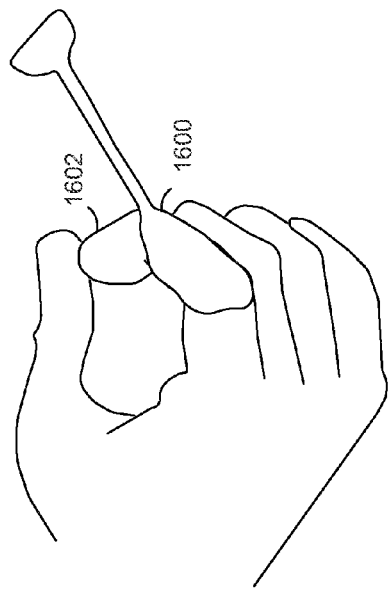
FIG. 16 is a perspective view of a custom-cut electrode positioned on a patient's finger.

FIG. 16 is a perspective view of a custom-cut electrode 1600 positioned on a patient's finger 1602. In some implementations, the unibody electrodes described herein (which include an electrode body and an electrode tail formed integrally from a continuous piece of conductive material) can be cut by a clinician or patient to fit the particular contours of a patient's tissue. For example, a clinician can use a standard pair of scissors to cut the electrode 1600 of FIG. 16 from a larger electrode (e.g., the electrodes of FIGS. 1 and 3) to fit a treatment area on a patient's finger 1602. Conventional electrodes, which include a multi-strand tail fanned to form various contact points on a conductive polymer, cannot be cut in this fashion with risking damage to the fanned strands. The electrodes described herein improve the delivery of electrostimulation by allowing clinicians to customize the shape and size of an electrode to a patient's unique contours and treatment goals.

Figure 17:
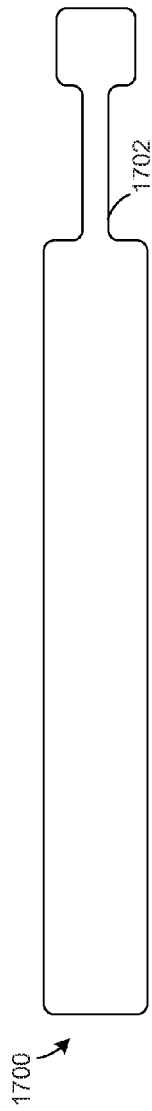
FIGS. 17 and 18 are plan views of two ribbon electrodes.
Figure 18:
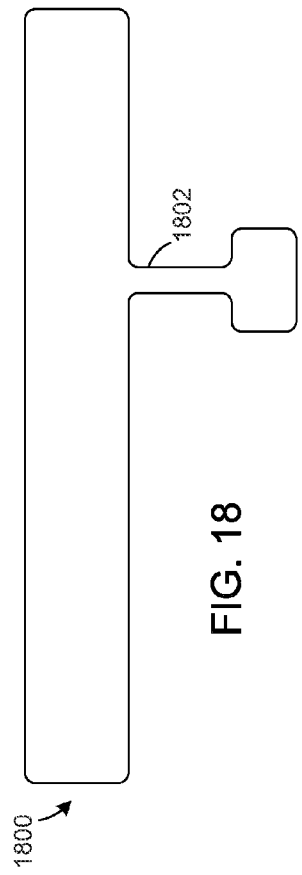

FIGS. 17 and 18 are plan views of two ribbon electrodes 1700 and 1800, respectively. Each of these electrodes includes a conductive layer with an integrally formed tail. In some implementations, the dimensions of the body of the electrodes 1700 and 1800 are approximately ¾" by 5", though any other dimensions may be used. The tail 1702 of the electrode 1700 of FIG. 17 is oriented longitudinally with respect to the primary axis of the electrode 1700, while the tail 1802 of the electrode 1800 of FIG. 18 is oriented perpendicularly with respect to the primary axis of the electrode 1800.

Ribbon electrodes such as these may be wrapped around a portion of a patient's body, such as a wrist or knee. The unitary construction techniques described herein allow the fabrication of electrodes with extended shapes, such as the ribbon electrodes 1700 and 1800, without risking dissimilar metal corrosion or hotspots resulting from fanned metal connections.

FIG. 19A is a cross-sectional view of a portion of an electrode body 1900 (which may be used with any of the electrodes described herein). A nonconductive top layer 1904 is disposed above a conductive layer 1906 to cover the conductive layer 1906. Additional conductive and nonconductive layers may also be included in the electrode body 1900 (or any other electrode body) but are not shown in FIG. 19A for ease of illustration. A gel layer 1908 is disposed below the conductive layer 1906 and a gel coating 1910 contiguous with the gel layer 1908 extends around the side of the body 1900 to cover the perimeter side surfaces 1902 of the conductive layer 1906. The presence of the gel coating 1910 on the perimeter side surfaces 1902 helps prevent electrical current from bypassing the gel coating 1910 or the gel layer 1908 and entering a patient's or clinician's tissue directly, which could cause a painful shock or an uneven distribution of current. The configuration of the gel coating 1910 depicted in FIG. 19A may be achieved by die cutting electrodes from layers of material, for example.

FIG. 19B is a cross-sectional view of an electrode tail 1920 (which may be used with any of the electrodes described herein, for example, as a unitary extension of an electrode body). The electrode tail 1920 includes a nonconductive top layer 1922, a conductive layer 1924 and a nonconductive bottom layer 1926. Additional conductive and nonconductive layers may also be included in the electrode tail 1920, but are not shown in FIG. 19B for ease of illustration. The electrode tail 1920 also has left perimeter side surface 1928a and right perimeter side surface 1928b. An insulating coating 1930 is disposed along the perimeter side surfaces 1928 to help prevent inadvertent electrical contact between a patient or clinician and the conductive layer 1924 along the sides of the electrode tail 1920, or between the conductive layer 1924 and another electrically-exposed surface (such as the tail of another electrode). As shown, the insulating coating 1930 has a left coating area 1930a that covers the left perimeter side surface 1928a and a right coating area 1930b that covers the right perimeter side surface 1928b. In some implementations, the insulating coating 1930 is a silicone applied in liquid form.

Automated manufacturing processes may be used to form the electrodes described herein. In some implementations, electrodes are formed with rotary conversion machinery, which fabricates electrodes from roll stock by dispensing adhesive, laminating, and cutting, among other operations. A second automated manufacturing process may be used to form a connector (such as the connector 400 formed from the flared portion 408 of a unitary conductive tail 406 depicted in FIGS. 4A-4C) or attach a connector (such as the connector housing 120 with the undulating receptacle 122 depicted in FIGS. 2A-2B, or the connectors 1506 depicted in FIGS. 15A-15B).

FIG. 20A is an exploded view of a stimulation system 2000 with an electronics layer 2012. Like the electrode system 1200 of FIG. 12, the stimulation system 2000 includes a plurality of electrode structures. In particular, the stimulation system 2000 includes a nonconductive top layer 2002, a first electrode 2004, an insulating layer 2006, a second electrode 2008 and a gel layer 2010 having a first gel segment 2010a and a second gel segment 2010b of a gel layer 2010. The first electrode 2004 and the second electrode 2008 are constructed as described above with reference to the corresponding structures of FIG. 12, as are the nonconductive top layer 2002, the insulating layer 2006 and the gel layer 2010. Unlike the electrode system 1200 of FIG. 12, the stimulation system 2000 includes an electronics layer 2012 disposed below the nonconductive top layer 2002 and the first electrode 2004. A nonconductive layer 2026 is disposed between the electronics layer 2012 and the first electrode 2004; in some implementations, the nonconductive layer 2026 takes the form of a coating of a nonconductive material (such as a nonconductive plastic) on the bottom surface of the electronics layer 2012 or the top surface of the first electrode 2004.

The electronics layer 2012 includes circuitry for performing one or more electrostimulation treatments. In some implementations, the electronics layer 2012 includes a printed circuit board configured with passive and active electrical components to perform a predetermined or programmable electrostimulation protocol. These electrical components may include one or more control microprocessors configured with machine-executable logic to control the conversion of energy from one or more power supplies included in the electronics layer 2012 (such as printed or coin cell batteries) into electrostimulation currents that may be driven into a patient's tissue through one or both of the first electrode 2004 and the second electrode 2008. The electronics layer 2012 may include printed traces of an electrically conductive material on one or more sub-layers (not shown) that connect the circuit components. Among the circuit components included in the electronics layer 2012 is a pulse generator 2024. The pulse generator 2024 generates two different channels of electrical signals that are transmitted to a patient's tissue via the first electrode 2004 and the second electrode 2008, respectively. Various illustrative implementations of pulse generators are described below with reference to FIGS. 21-24.

In the stimulation system 2000, the electronics layer 2012 is electrically connected to the first electrode 2004 via contact points 2014a (in the electronics layer 2012) and 2016a (in the first electrode 2004). These contact points 2014a and 2016a are electrically connected by a puncture technique, in which the contact point 2014a of the electronics layer 2012 is aligned with and positioned adjacent to the contact point 2016a of the first electrode 2004, and the electronics layer 2012 and the first electrode 2004 are punctured at the contact points 2014a and 2016a to form an electrical connection between conductive materials included in the electronics layer 2012 and the first electrode 2004. In some implementations, the puncture connections are formed by pushing a pin, rod, or other rigid member through a conductive portion of the electronics layer 2012 to deform the conductive portion and form a hole surrounded by protrusions of the conductive material extending away from the electronics layer 2012. In some implementations, these protrusions are jagged and irregular, while in other implementations, the body of the conductive layer is pre-scored or otherwise prepared so that the protrusions are more regularly spaced and sized. When the electronics layer 2012 is separated from the first electrode 2004 by the nonconductive layer 2026, the protrusions extend through the nonconductive layer 2026 and can be bent to fold back against the first electrode 2004 to form an electrical connection between the conductive portion of the electronics layer 2012 and the first electrode 2004. In some implementations, the electronics layer 2012, the nonconductive layer 2026 and the first electrode 2004 are stacked, and the puncturing operation is applied to the entire stack.

Because the electronics layer 2012 is separated from the first electrode 2004 at all points other than the puncture locations by the nonconductive layer 2026, the puncture between the contact points 2014a and 2016a will allow electrical signals generated by an appropriate channel of the pulse generator 2024 (e.g., a first channel) to flow to the first electrode 2004 without short-circuiting the remaining components in the electronics layer 2012. Although only one contact point between the electronics layer 2012 and the first electrode 2004 is shown in FIG. 20, any number of contact points may be used. The stimulation system 2000 also includes a nonconductive element 2018a positioned below the contact point 2016a, which may prevent the formation of hotspots within the gel layer 2010 as discussed above.

One or more sets of similar contact points may be provided. As shown in FIG. 20A, a second set of contact points 2014b and 2016b is included in the electronics layer 2012 and the second electrode 2008, respectively. The electrical signals generated on a second channel of the pulse generator 2024 are transmitted to the second electrode 2008. The contact points 2014b and 2016b are connected using the puncture technique described above. The stimulation system 2000 also includes a nonconductive element 2018b positioned below the contact point 2016b. FIG. 20B is a cross-sectional view of the stimulation system of FIG. 20A. Although two electrodes and a single electronics layer are illustrated in FIG. 20, any number of electrodes and any number of electronics layers, arranged in any desired orientation, may be used (such as any of the electrode systems described herein). Using this connection structure, different output channels of the pulse generator 2024 may be directed to different electrodes within the stimulation system 2000 without the use of bulky wires or the need for hand-soldering. In some implementations, the puncture connections are formed by rotary converting equipment acting on rolls of material that provide the electronics layer 2012, the first and second electrodes 2004 and 2008, respectively, and the nonconductive layer 2026. Automation of the puncture connection process, as well as other steps in the production of the electrodes and systems described herein, may enable the effective fabrication of previously infeasible structures and may improve the quality of the manufactured items. For example, an automated electrode manufacturing process may be more readily monitored (e.g., using cameras and other sensors) than a manual assembly process, which may enable earlier detection of manufacturing errors thereby preventing unsuitable electrodes from entering the marketplace.

The electronics layer 2012 also includes the electrical switches 2022a, 2022b and 2022c. These electrical switches are components that provide an electrical response to forces exerted on the surface of the switches, and are commonly used in user interface design for registering button presses or other user inputs. Three buttons 2020a, 2020b and 2020c are disposed above the electrical switches 2022a, 2022b and 2022c, respectively, and are aligned with the apertures 2018a, 2018b and 2018c, respectively, in the nonconductive top layer 2002. The electrical switches 2022a, 2022b and 2022c are in electrical communication with a microprocessor or other circuitry included in the electronics layer 2012 and are used to initiate or adjust the electrostimulation provided by the stimulation system 2000. As shown in FIG. 20A, the power button 2020b, marked "ON," may be pressed by a user or clinician to activate the power switch 2022b to initiate (and possibly to terminate) an electrostimulation treatment. The buttons 2020a and 2020c are marked with "+" and "−" symbols, respectively, to indicate that a patient or clinician may use those buttons to activate the intensity adjustment switches 2022a and 2022c to adjust up and down, respectively, the intensity of the electrostimulation provided by the stimulation system 2000 (e.g., changing the amplitude or frequency of a generated stimulation current). Additional user interfaces that may be implemented instead of or in addition to the keys 2020a, 2020b and 2020c are described in Mueller et al., U.S. Patent Application Publication No. 2010/0042180, incorporated by reference herein in its entirety.

The circuitry included in the electronics layer 2012 of the stimulation system 2000 may be configured to generate one or more electrostimulation protocols (i.e., a predefined current or voltage waveform). These electrostimulation protocols may be stored in a memory (such as an EEPROM) included in the electronics layer 2012, or may be encoded into the circuitry using logic gates or other circuitry (e.g., an ASIC). In some implementations, the stimulation system 2000 is configured to provide a single electrostimulation protocol when the power button 2020b is pressed (e.g., a particular TENS therapy or a particular iontophoretic treatment). The single electrostimulation protocol may be directed to treating a particular condition (e.g., pain or muscle tension), and the stimulation system 2000 may be packaged and provided to clinicians and patients as a treatment for the particular condition along with instructions on how to position to stimulation system 2000 on the patient's tissue. The stimulation system 2000 can then be activated and the electrical treatment delivered by depressing the power button 2020b. In some implementations, the stimulation system 2000 can only be used a predetermined number of times before the stimulation system 2000 will no longer respond to presses of the power button 2020b. The number of times that the stimulation system 2000 has been turned on may be stored in an EEPROM or other memory included in the electronics layer 2012, and a microprocessor may be configured to count up or down to a fixed value that represents the maximum number of uses. In some implementations, the electrostimulation protocols may provide for electrostimulation treatment over a predetermined period of time (e.g., thirty minutes). The time period may be enforced by timer circuitry included in the electronics layer 2012, or by a chemical or other switch in the electronics layer 2012.

In some implementations, the circuitry included in the electronics layer 2012 of the stimulation system 2000 may be configured to provide an iontophoretic treatment followed by a TENS treatment. In such implementations, the gel segments 2010a and 2010b are replaced with drug delivery reservoirs that contain charged compounds that are drive from the reservoirs into a patient's skin when a DC current is applied via the first and second electrodes 2004 and 2008. The drug delivery reservoirs may contain, for example, a drug delivery matrix in which the therapeutic compounds are suspended.

FIG. 21 is a flow diagram illustrating the operation of a stimulation system (such as the stimulation system 2000 of FIG. 20) configured to deliver iontophoretic and TENS therapy. At step 2102, the stimulation system 2000 delivers an iontophoretic treatment by applying an electric field to drive a therapeutic compound into the patient's tissue. When the stimulation system 2000 detects that the iontophoretic treatment time has elapsed at step 2104, the stimulation system 2000 begins to deliver a TENS treatment. As discussed above, the stimulation system 2000 may determined that the iontophoretic treatment time has elapsed at step 2104 using timer circuitry included in the electronics layer 2012, or by a chemical or other switch in the electronics layer 2012.

The delivery of the iontophoretic treatment and the TENS treatment may take place using the same sets of electrodes (i.e., the first electrode 2004 and the second electrode 2008), but by applying different waveforms to those electrodes. FIG. 22 depicts an illustrative waveform 2200 generated by the stimulation system 2000 to provide iontophoretic treatment during a first portion 2200a of the waveform 2200 and a TENS treatment during a second portion 2200b of the waveform 2200. The first portion 2200a is a DC portion, representing the one-way flow of current between the first electrode 2004 and the second electrode 2008 over the time period $T_1$. The first portion 2200a of the waveform 2200 provides the electric field that drives the therapeutic compound into the patient's tissue. The iontophoretic treatment is illustrated in FIG. 23A, in which current is applied in one direction (indicated by the arrows 2310) between the first electrode 2004 (and its corresponding reservoir 2302) and the second electrode 2008 (and its corresponding reservoir 2304) through the patient's tissue 2308. As a result, the therapeutic compound 2306 is driven into the patient's tissue 2308.

When the stimulation system 2000 determines that the iontophoretic treatment time has ended (represented with the vertical line 2202 in FIG. 22), the circuitry included in the electronics layer 2012 of the stimulation system 2000 begins to generate an AC waveform. In some implementations, this circuitry includes an H-bridge transistor configuration. The second portion 2200b shown in FIG. 22 is a square, biphasic, symmetric waveform, but other AC waveforms may also be used. The TENS treatment is illustrated in FIG. 23B, in which current is applied in two directions (indicated by the arrows 2310 and 2312) between the first electrode 2004 (and its corresponding reservoir 2302) and the second electrode 2008 (and its corresponding reservoir 2304) through the patient's tissue 2308. In preferred implementations, the TENS portion of the waveform has no DC component so that the stimulation system does not transfer any therapeutic compound remaining in the reservoirs after the iontophoretic treatment time has been reached. Additionally, the presence of residual compound may improve the conductivity of the interface between the electrodes of the stimulation system and the patient's tissue.

In preferred implementations, the same power source (e.g., a battery) that provides the energy for the iontophoretic treatment (at step 2012 of FIG. 21) is used to provide the energy for the TENS treatment (at step 2106 of FIG. 21). In some existing iontophoretic devices, additional battery power may remain after the iontophoretic treatment is complete; when these devices are disposable, the batteries are thrown away and this energy is lost. In contrast, in stimulation systems configured to operate according to the process of FIG. 21, the remaining power in the battery may be used for the generation of current for TENS therapy, which may continue until the battery is depleted or a predetermined stop time has been reached. Devices so configured may be especially beneficial to patients who are receiving iontophoresis therapy to treat pain, in which case a pain-relief TENS treatment following the iontophoretic treatment may further reduce the patient's discomfort. Additionally, applying a TENS treatment using the same physical device as an iontophoretic treatment improves on existing technologies by reducing the skin irritation associated with the removal and application of multiple devices and eliminating the risk that the iontophoretic and TENS treatments will be incorrectly positioned in different locations on the patient's body.

Figure 24:
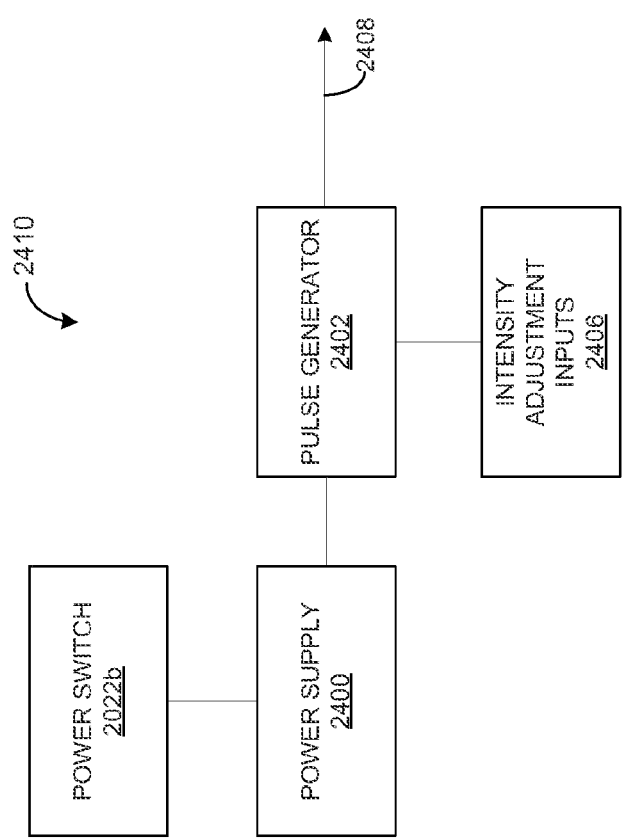
FIG. 24 is a block diagram of illustrative circuitry that may be included in the electronics layer of the stimulation system of FIG. 20.

FIG. 24 is a block diagram of illustrative circuitry 2010 that may be included in the electronics layer 2012 of the stimulation system 2000 of FIG. 20. The circuitry 2010 includes a power supply 2400, a pulse generator 2402, a power switch 2404, intensity adjustment inputs 2406, and an output 2408. The power supply 2400 provides electrical power to the circuitry 2010 and may include, for example, one or more printed or coin cell batteries. In some embodiments, the power supply 2400 also includes power filtering and/or voltage adjustment circuitry. The power supply 2400 is electrically coupled to the power switch 2022b (FIG. 20) and to the pulse generator 2402. The power switch 2022b receives input from a user through the power button 2020b (FIG. 20) and operates with power supply 2400 to supply power to the circuitry 2010.

The pulse generator 2402 generates electrical signals that are transmitted to a patient's tissue via the first electrode 2004 and the second electrode 2008 (FIG. 20). The pulse generator 2402 is electrically coupled to a two-channel output 2408 and provides the electrical signals to the two-channel output 2408. In turn, each of the channels of the two-channel output 2408 is electrically coupled to one of the first electrode 2004 and the second electrode 2008 (FIG. 20) in order to deliver the electrical signals to the therapeutic location of the patient. The intensity adjustment inputs 2406 (including intensity adjustment switches 2022a and 2022c of FIG. 20) are electrically coupled to the pulse generator 2402 and receive input from the user through intensity adjustment buttons 2020a and 2020c (FIG. 20). The intensity adjustment inputs 2406 operate with the pulse generator 2402 to adjust the intensity of the electrical signals sent to the two-channel output 2408. Some examples of suitable pulse generators are described in U.S. Pat. Nos. 4,887,603 and 4,922,908, both by Morawetz et al., incorporated by reference herein in their entireties. In some embodiments, the electrical signals generated by the pulse generator 2402 are simple modulated pulse (SMP) signals. Other configurations and electrical signals are possible.

FIG. 25 is an electrical schematic of a circuit 2500 that may be used to implement the circuitry 2410 of FIG. 24. The circuit 2500 includes a power supply 2500, a pulse generator 2502, a power switch 2504, an amplitude adjustment switch 2506, and an output 2508. The power supply 2500 includes a battery 2512, a thermistor 2514, a step-up converter 2516, and other electrical components. The power supply 2500 is electrically coupled to the pulse generator 2502 and supplies power thereto. In addition, the power supply 2504 is shown as electrically coupled to the connector block 2520 that is used to supply power to the power supply 2500 to charge battery 2512. Charging energy may come from, for example, a home or commercial power supply, such as available through an electrical power outlet, or a vehicle power supply, such as accessible through a 12V receptacle. The thermistor 2514 is electrically coupled between the battery 2512 and the connector block 2520 and is used to detect the temperature of the battery 2512 to ensure that the battery 2512 is not overheated while recharging. In some implementations (including those intended for disposable applications), the power supply included in the electronics layer 2012 of the stimulation system 2000 of FIG. 20 is not rechargeable, in which case the components of the circuit 2500 that provide the rechargeability function are not included.

The power switch 2504 is used to turn the circuitry 2500 on or off. The power switch 2504 may be easily controlled, for example, by the power button 2020b of FIG. 20, as described above. In some implementations, the power switch 2504 is a single-pole double-throw (SPDT) switch, as shown. The power supply 2500 also includes a step-up converter 2516, which operates to increase the voltage level of the power supplied by the battery 2512 to a desired voltage level. The pulse generator 2502 receives power from the power supply 2500 and generates a electrical signal. The electrical signal is provided by the pulse generator 2502 to the output 2508. The pulse generator 2502 includes an amplitude adjustment switch 2506. The amplitude adjustment switch 2506 may be easily controlled, for example, by the intensity adjustment buttons 2020a and 2020c of FIG. 20. In this embodiment, the amplitude adjustment switch 2506 is a potentiometer. When the potentiometer is adjusted, the intensity of the electrical signal generated by the pulse generator 2502 is increased or decreased accordingly. The pulse generator 2502 includes first and second timers 2530 and 2532, as well as additional circuitry as shown in FIG. 25.

The pulse generator 2502 also includes an output stage 2540. For ease of illustration, the output stage 2540 depicted in FIG. 25 only depicts the output for one channel (i.e., the output that will be provided to one of the first electrode 2004 and the second electrode 2008), but a second output channel is implemented in the same manner. The output stage 2540 includes a MOSFET 2542 and a transformer 2544. The output stage 2540 acts to increase the output voltage of the electrical signal before sending the electrical signal to the output 2508, where it will be electrically coupled to an electrode for delivery to a patient's tissue.

Figure 26:
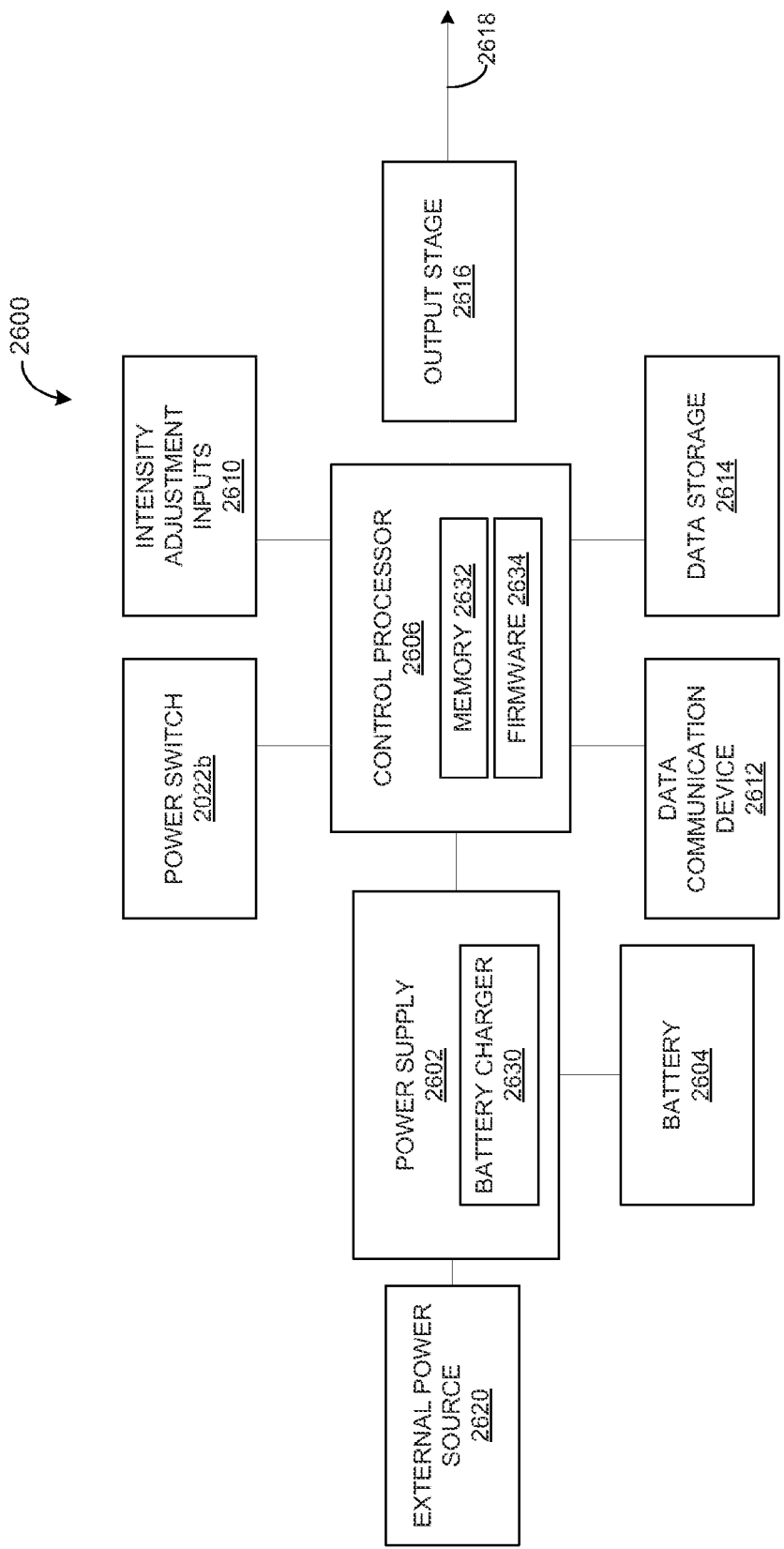
FIG. 26 is a block diagram of other illustrative circuitry that may be included in the electronics layer of the stimulation system of FIG. 20.

FIG. 26 is a block diagram of illustrative circuitry 2600 that may be included in the electronics layer 2012 of the stimulation system 2000 of FIG. 20. In this implementation, the circuitry 2600 is formed from primarily digital circuitry. The circuitry 2600 includes a power supply 2602, a battery 2604, a controller processor 2606, a power switch 2025b (FIG. 20), intensity adjustment inputs 2610, a data communication device 2612, a data storage device 2614, an output stage 2616, and an output 2618. During operation, the power supply 2602 receives power from the battery 2604. The power supply 2602 converts the battery power to a desired voltage before supplying the power to other components of the circuitry 2600. The power supply 2602 also includes a battery charger 2630. The battery charger 2630 receives power from external power source 2620, to charge the battery 2604. As described above with reference to FIG. 25, in some implementations, the power supply included in the electronics layer 2012 of the stimulation system 2000 of FIG. 20 is not rechargeable, in which case the components of the circuitry 2600 that provide the rechargeability function are not included.

The control processor 2606 controls the operation of the circuitry 2600. The control processor 2606 is powered by the power supply 2602, and generates electrical signals that are provided to the output stage 2616. The control processor 2606 is also electrically coupled to the power switch 2022b and intensity adjustment inputs 2610. The control processor 2606 monitors the state of the power switch 2022b. When the control processor 2606 detects that the state of the power switch 2022b has changed (e.g., in response to a user pressing the power button 2020b of FIG. 20), the control processor 2606 turns the circuitry 2600 on or off accordingly. The control processor 2606 also monitors the state of the intensity adjustment inputs 2610 (e.g., the intensity adjustment switches 2022a and 2022c of FIG. 20). When the control processor 2606 detects that the state of the intensity adjustment inputs 2610 has changed (e.g., in response to a user pressing the intensity adjustment buttons 2020a and 2020b of FIG. 20), the control processor 2606 increases or decreases the intensity of electrical signals provided to the output stage 2616 accordingly.

The control processor 2606 includes a memory 2632, which stores computer-readable firmware 2634. The firmware 2634 includes software commands and algorithms that are executed by the control processor 2606 and defines logical operations performed by the control processor 2606. The software commands and algorithms in the firmware 2634 may be used to operate the electrical stimulation device in a desired mode, such as a mode that provides transcutaneous electrical nerve stimulation therapy or a mode that provides muscular stimulation therapy. In some implementations, the circuitry 2600 includes a data communication device 2612. Data communication devices include wired or wireless communication devices, such as serial bus communication devices (e.g., a Universal Serial Bus communication devices), local area networking communication devices (e.g., an Ethernet communication device), a modem, a wireless area networking communication device (e.g., an 802.11x communication device), a wireless personal area networking device (e.g., a Bluetooth™ communication device), or other communication device. The data communication device 2612 can be used to send and receive data with another device. For example, the data communication device 2612 can be used to download a different version of the firmware 2634 to the circuitry 2600 to alter the operation of the control processor 2606, and operate the stimulation system 2000 of FIG. 20 in a desired mode, such as a mode that provides iontophoresis therapy. In certain embodiments, a firmware algorithm must be purchased before it can be downloaded by a user. In certain embodiments, the a user must access a patient interface of a web server or other similar interface before downloading a firmware algorithm. The circuitry 2600 also includes a data storage device 2614, such as a memory card or other known data storage device. In some implementations, the data storage device 2614 is part of the memory 2632. The data communication device 2612 can also be used to upload data to another device. For example, the control processor 2606 may store a electrostimulation delivery log in the data storage device 2614. The control processor 2606 can be used to upload the therapy log to an external device by sending the data log to the data communication device 2612.

When the circuitry 2600 is on, the control processor 2606 generates therapeutic electrical signals, and provides those signals to the output stage 2616. The output stage 2616 converts and filters the electrical signals, and then provides the electrical signals to the output 2618. The output 2618 is electrically coupled to one of the first electrode 2004 and the second electrode 2008 of the stimulation system 2000 of FIG. 20, which thereby delivers electrical signals to the patient's tissue. As discussed above with reference to FIG. 25, for ease of illustration, FIG. 26 only depicts the output for one channel (i.e., the output that will be provided to one of the first electrode 2004 and the second electrode 2008), but a second output channel is implemented in the same manner.

Figures 1, 27:
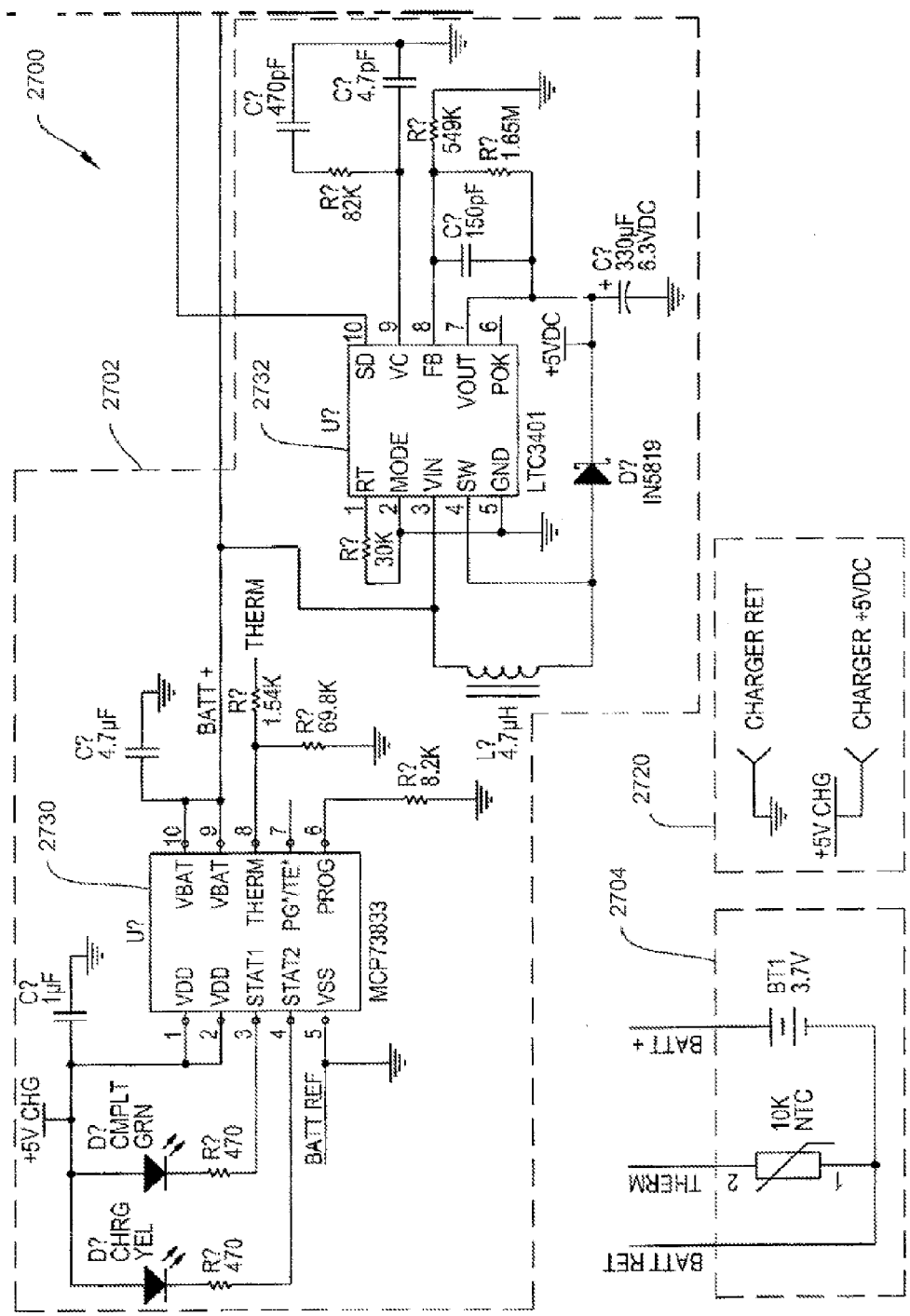
Figures 2, 27:
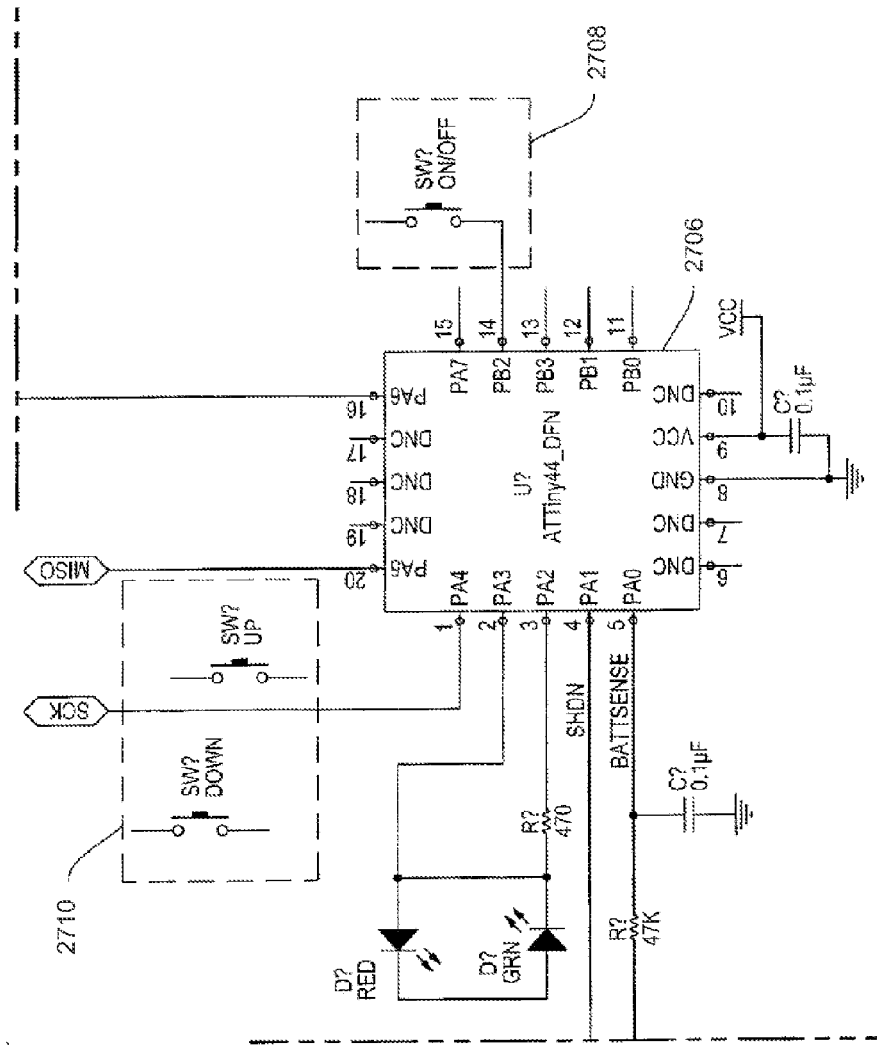
Figures 3, 27:
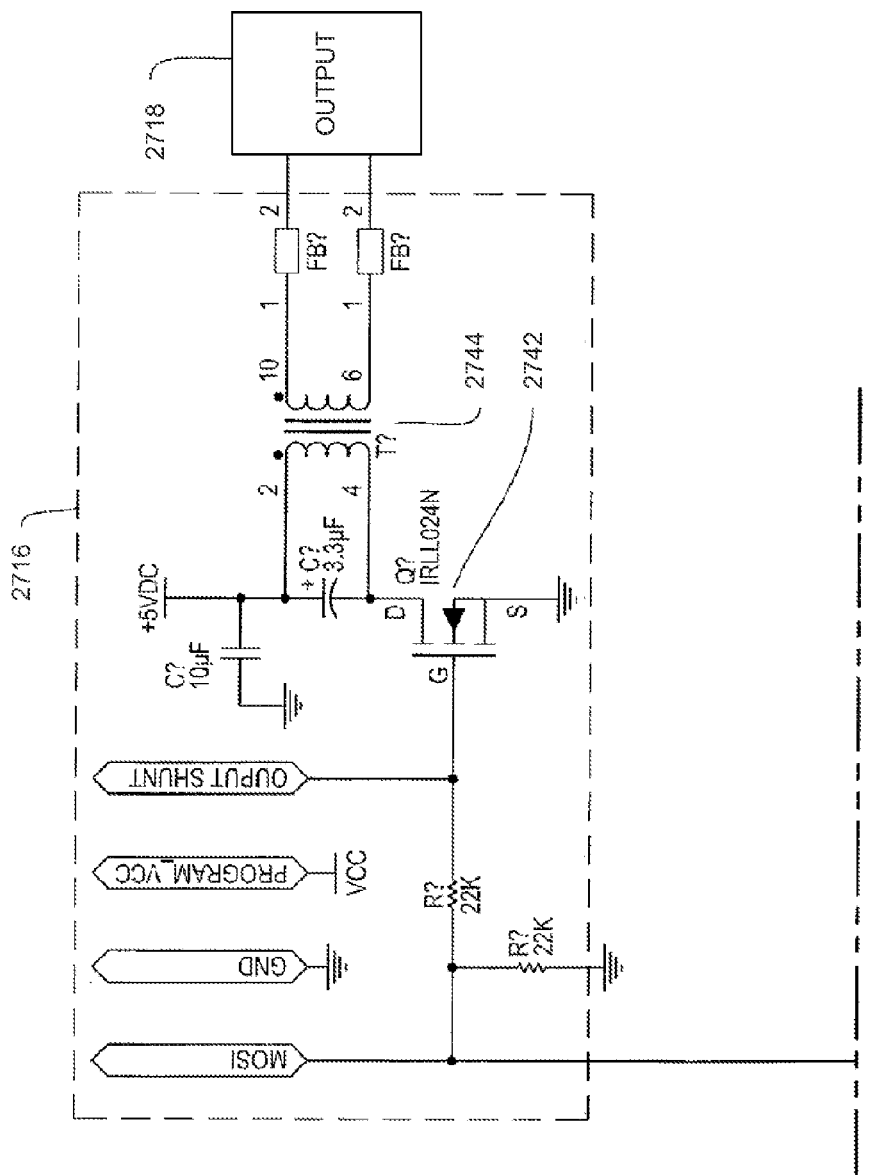
Figure 28B:
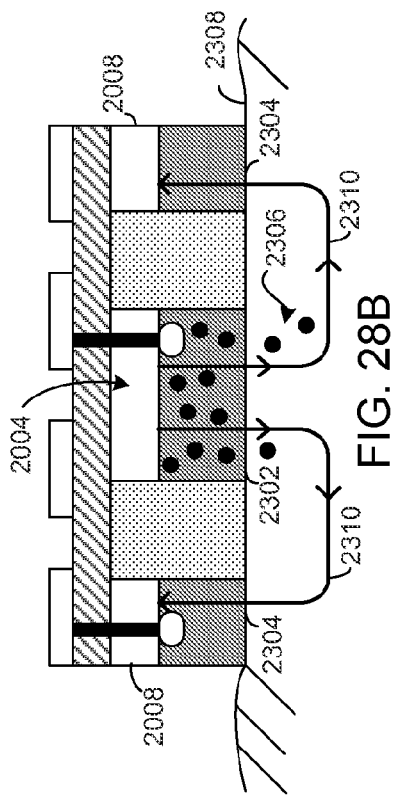
FIG. 28B corresponds to a cross-sectional view of the iontophoresis delivery system of FIG. 28A when driving a therapeutic compound into a patient's tissue.
Figure 28C:
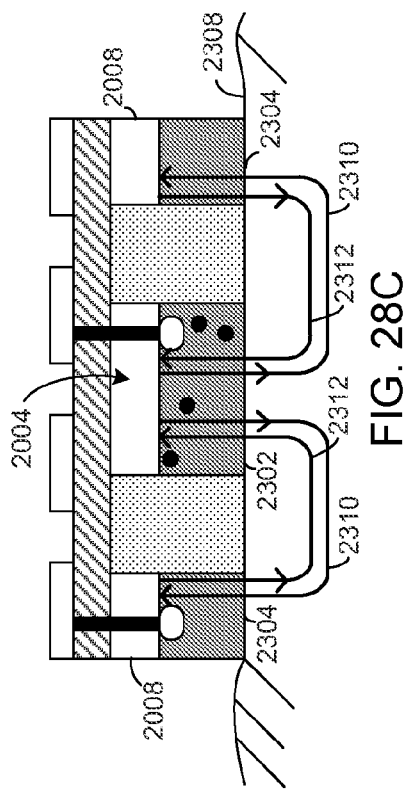
FIG. 28C corresponds to a cross-sectional view of the iontophoresis delivery system of FIG. 28A when delivering a TENS treatment.
Figure 28A:
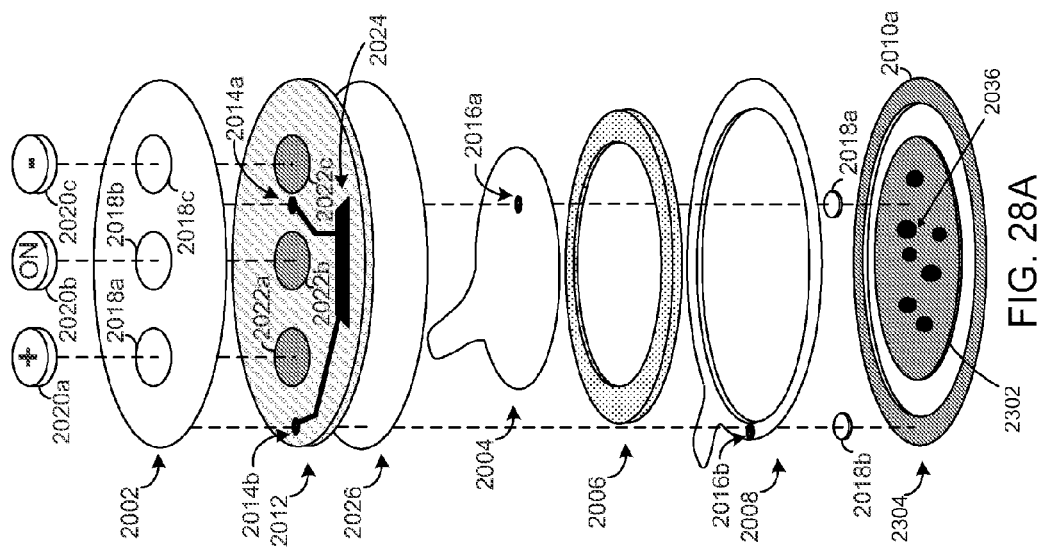
FIG. 28A is an exploded view of an iontophoresis delivery system.

FIG. 27 is an electrical schematic of circuitry 2700 that may be used to implement the circuitry 2600 of FIG. 26. The circuitry 2700 includes a control processor 2706 that controls the operation of the circuitry 2600, and also includes a power supply 2702, a battery 2704, a power switch 2708, amplitude adjustment switches 2710, an output stage 2716, and an output 2718. The circuitry 2700 can also be connected to an external power source 2720 that may be used to charge the battery 2704, as described above. The battery 2704 (which may be a lithium-ion battery) provides power to the power supply 2702. The power supply 2702 includes a lithium-ion charge management controller 2730 (available as an off-the-shelf component) and a step-up converter 2732, as well as other electrical components as shown. Power supply 2702 can also be connected to external power source 2720, such as a 5V DC power source, as described above. In some implementations in which the battery 2704 is rechargeable, the battery 2704 includes a thermistor to monitor the temperature of the battery 2704 during charging.

The control processor 2706 controls the operation of the circuitry 2700. The control processor 2706 may include an 8-bit microprocessor, or one or more other processing devices such as other microprocessors, central processing units (CPUs), microcontrollers, programmable logic devices, field programmable gate arrays, digital signal processing (DSP) devices, and the like. The control processor 2706 may be of any general variety such as reduced instruction set computing (RISC) devices, complex instruction set computing devices (CISC), or specially designed processing devices such as an application-specific integrated circuit (ASIC) device.

The control processor 2706 is electrically coupled to the power switch 2708 and the amplitude adjustment switches 2710. The power switch 2708 provides signals to the control processor 2706 that cause the control processor 2706 to alternate the circuitry 2700 between on and off states accordingly. The amplitude adjustment switches 2710 provide electrical signals to the control processor 2706 that the control processor 2706 uses to adjust the intensity of the electrical signals generated by the circuitry 2700. Electrical signals generated by the control processor 2706 are passed to the output stage 2716.

The output stage 2716 converts the electrical signals received from the control processor 2706 to an appropriate form and then provides the electrical signals to the output 2718. For ease of illustration, the output stage 2716 depicted in FIG. 27 only depicts the output for one channel (i.e., the output that will be provided to one of the first electrode 2004 and the second electrode 2008 of the stimulation system 2000 of FIG. 20), but a second output channel is implemented in the same manner. As shown, the output stage 2716 includes a MOSFET 2742 and a transformer 2744. Other implementations do not include the transformer 2744, but rather use a flyback converter or other converter to generate an appropriate output signal.

It is to be understood that the foregoing description is merely illustrative, and is not to be limited to the details given herein. While several embodiments have been provided in the present disclosure, it should be understood that the disclosed systems, devices and methods and their components may be embodied in many other specific forms without departing from the scope of the disclosure.

Variations and modifications will occur to those of skill in the art after reviewing this disclosure, where disclosed features may be implemented in any combination and subcombinations (including multiple dependent combinations and subcombinations), with one or more other features described herein. The various features described or illustrated above, including any components thereof, may be combined or integrated in other systems; moreover, certain features may be omitted or not implemented.

Examples of changes, substitutions and alterations are ascertainable by one skilled in the art and to be made without departing from the scope of the information disclosed herein. All references cited herein are incorporated by reference in their entirety and made part of this application.

What is claimed is:

1. An iontophoresis delivery system comprising:
an insulating layer;
a nonconductive top layer;
a nonconductive bottom layer;
a first nonconductive element;
a second nonconductive element;
a first electrode, wherein the first electrode is situated between the nonconductive bottom layer and the insulating layer;
a second electrode, wherein the first electrode and the second electrode are spaced apart from each other, wherein the second electrode is ring-shaped and wherein the first electrode is within an interior of the second electrode;
a first electrode reservoir comprising a therapeutic compound, the first electrode reservoir configured to deliver the therapeutic compound into a patient's tissue when a DC current is driven into the patient's tissue from the first electrode to the second electrode;
a second electrode reservoir;
and wherein the second electrode is situated between the insulating layer and the second electrode reservoir; and
an electronics layer situated between the nonconductive top layer and the nonconductive bottom layer, the electronics layer having a first electronics layer contact point in electrical contact and alignment with a first electrode contact point in the first electrode via a first puncture connection and a second electronics layer contact point in electrical contact and alignment with a second electrode contact point in the second electrode via a second puncture connection, wherein the electronics layer, the nonconductive bottom layer and the first electrode are assembled in a stack, and wherein the stack is punctured to form the puncture connections, wherein the first nonconductive element is positioned below the first electrode contact point and wherein the second nonconductive element is positioned below the second electrode contact point, the electronics layer further comprising pulse generation circuitry configured to:
deliver the DC current to the first electrode for a predetermined period of time to drive the therapeutic compound into the patient's tissue;
after delivering the DC current for the predetermined period of time, deliver an AC TENS current from the second electrode to the first electrode.

2. The iontophoresis delivery system of claim 1, further comprising a battery, wherein the pulse generation circuitry is configured to use the battery to power the delivery of the DC current and the delivery of the AC TENS current.

3. The iontophoresis delivery system of claim 1, wherein the electronics layer comprises timer circuitry configured to indicate that the predetermined period of time has elapsed when a predetermined amount of therapeutic compound has been driven into the patient's tissue.

4. The iontophoresis delivery system of claim 1, wherein the first electrode comprises a conductive polyvinylchloride or polyurethane impregnated with carbon.

5. The iontophoresis delivery system of claim 1, wherein the first electrode is circle-shaped.

6. The iontophoresis delivery system of claim 1, wherein the electronics layer comprises at least one electrical switch configured to provide an electrical response to a force exerted on a surface of the at least one switch so as to register a button press by a button disposed above the at least one electrical switch and aligned with an aperture in the nonconductive top layer, wherein the at least one electrical switch is in electrical communication with a microprocessor or other circuitry included in the electronics layer configured to initiate or adjust at least one of the DC current or the AC TENS current.

7. The iontophoresis delivery system of claim 1, wherein the electronics layer comprises three electrical switches, wherein each electrical switch is configured to provide an electrical response to a force exerted on a surface of the electrical switch, the system further comprising a button disposed above each of the three electrical switches, the nonconductive top layer comprising three apertures, wherein each button is aligned with one of the apertures.

8. The iontophoresis delivery system of claim 7, wherein one of the buttons is configured to activate the power switch so as to initiate or terminate an electrostimulation treatment, wherein one of the buttons is configured to activate an intensity adjustment switch configured to adjust an intensity of the electrostimulation up, and wherein one of the buttons is configured to activate an intensity adjustment switch configured to adjust an intensity of the electrostimulation down.

9. The iontophoresis delivery system of claim 8, wherein the intensity is adjusted by changing an amplitude or a frequency of a generated stimulation current.

10. The iontophoresis delivery system of claim 1, wherein the pulse generation circuitry is configured to apply AC TENS current in two directions between the first electrode and the second electrode, and wherein a waveform of the AC TENS current has no DC component so as not to transfer any therapeutic compound remaining in the first electrode reservoir after an iontophoretic treatment time has been reached.

11. The iontophoresis delivery system of claim 1, wherein the puncture connections are formed by pushing a pin, rod, or other rigid member through a conductive portion of the electronics layer to deform the conductive portion and form a hole surrounded by protrusions of the conductive material extending away from the electronics layer.

12. The iontophoresis delivery system of claim 11, wherein the protrusions are jagged and irregular.

13. The iontophoresis delivery system of claim 11, wherein a body of the conductive layer is pre-scored or otherwise prepared so that the protrusions are regularly spaced and sized.

14. The iontophoresis delivery system of claim 11, wherein the protrusions extend through the nonconductive layer and are bent to fold back against the first electrode to form an electrical connection between the conductive portion of the electronics layer and the first electrode.

* * * * *